US008338487B2

(12) United States Patent
Chen et al.

(10) Patent No.: US 8,338,487 B2
(45) Date of Patent: Dec. 25, 2012

(54) SUBSTITUTED ARYLAMINO-1,2,3,4-TETRAHYDRO NAPHTHALENES AND -2,3-DIHYDRO-1H-INDENES AS POTASSIUM CHANNEL MODULATORS

(75) Inventors: Huanming Chen, Irvine, CA (US); Jean-Michel Vernier, Laguna Niguel, CA (US)

(73) Assignee: Valeant Pharmaceuticals International, Inc., Aliso Viejo, CA (US)

( * ) Notice: Subject to any disclaimer, the term of this patent is extended or adjusted under 35 U.S.C. 154(b) by 0 days.

(21) Appl. No.: 13/098,176

(22) Filed: Apr. 29, 2011

(65) Prior Publication Data
US 2011/0207812 A1    Aug. 25, 2011

Related U.S. Application Data

(62) Division of application No. 11/810,114, filed on Jun. 4, 2007, now Pat. No. 7,960,436.

(60) Provisional application No. 60/811,463, filed on Jun. 5, 2006.

(51) Int. Cl.
C07C 235/16 (2006.01)
A61K 31/16 (2006.01)

(52) U.S. Cl. ........................................ 514/613; 564/123
(58) Field of Classification Search ........................ None
See application file for complete search history.

(56) References Cited

U.S. PATENT DOCUMENTS

| | | | |
|---|---|---|---|
| 4,181,803 A | 1/1980 | Morita et al. |
| 4,554,281 A | 11/1985 | vonBebenburg et al. |
| 4,668,684 A | 5/1987 | Tibes et al. |
| 4,778,799 A | 10/1988 | Tibes et al. |
| 4,923,858 A | 5/1990 | Engel et al. |
| 4,923,974 A | 5/1990 | Ueda et al. |
| 5,032,591 A | 7/1991 | Evans et al. |
| 5,162,346 A | 11/1992 | Lobisch et al. |
| 5,234,947 A | 8/1993 | Cherksey |
| 5,262,419 A | 11/1993 | Aberg et al. |
| 5,284,861 A | 2/1994 | Lobisch et al. |
| 5,384,330 A | 1/1995 | Dieter et al. |
| 5,428,039 A | 6/1995 | Cohen |
| 5,502,058 A | 3/1996 | Mayer et al. |
| 5,643,921 A | 7/1997 | Grover |
| 5,679,706 A | 10/1997 | D'Alonzo et al. |
| 5,760,007 A | 6/1998 | Shank |
| 5,800,385 A | 9/1998 | Demopulos et al. |
| 5,849,789 A | 12/1998 | Rostock et al. |
| 5,852,053 A | 12/1998 | Rostock et al. |
| 5,858,017 A | 1/1999 | Demopulos et al. |
| 5,860,950 A | 1/1999 | Demopulos et al. |
| 5,914,425 A | 6/1999 | Meisel et al. |
| 5,925,634 A | 7/1999 | Olney |
| 6,117,900 A | 9/2000 | Rundfeldt et al. |
| 6,211,171 B1 | 4/2001 | Sawynok et al. |
| 6,218,411 B1 | 4/2001 | Koga |
| 6,265,417 B1 | 7/2001 | Carroll |
| 6,281,211 B1 | 8/2001 | Cai et al. |
| 6,326,385 B1 | 12/2001 | Wickenden et al. |
| 6,348,486 B1 | 2/2002 | Argentieri et al. |
| 6,395,736 B1 | 5/2002 | Parks et al. |
| 6,451,857 B1 | 9/2002 | Hurtt et al. |
| 6,469,042 B1 | 10/2002 | Hewawasam et al. |
| 6,472,165 B1 | 10/2002 | Rundfeldt et al. |
| 6,495,550 B2 | 12/2002 | McNaughton-Smith et al. |
| 6,500,455 B1 | 12/2002 | Frantsits |
| 6,537,991 B1 | 3/2003 | Shaw et al. |
| 6,538,004 B2 | 3/2003 | Drizin |
| 6,538,151 B1 | 3/2003 | Meisel et al. |
| RE38,115 E | 5/2003 | Smith et al. |
| 6,589,986 B2 | 7/2003 | Bowlby et al. |
| 6,593,335 B1 | 7/2003 | Carroll |
| 6,642,209 B1 | 11/2003 | Fukunuga |
| 6,645,521 B2 | 11/2003 | Cassel |
| 6,737,422 B2 | 5/2004 | McNaughton-Smith et al. |
| 7,045,551 B2 | 5/2006 | Wu et al. |

(Continued)

FOREIGN PATENT DOCUMENTS

CA    2542434    5/2005

(Continued)

OTHER PUBLICATIONS

Armand et al., "Effects of retigabine (D-23129) on different patterns of epileptiform activity induced by 4-aminopyridine in rat entorhinal cortex hippocampal slices," *Naunyn-Schmiedeberg's Arch. Pharmacol.* 359:33-39 (1999).

Armijo et al., "Ion channels and epilepsy," *Curr. Pharm. Des.* 11:1975-2003 (2005).

Barhanin, M., et al., "$K_VLQT1$ and ISK (minK) proteins associate to form the $I_{Ks}$ cardiac potassium current," *Nature* 384(6604):78-80 (1996).

(Continued)

*Primary Examiner* — Zinna Northington Davis
(74) *Attorney, Agent, or Firm* — Jones Day

(57) ABSTRACT

This invention provides compounds of formula I

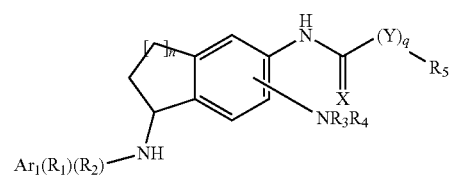

where $Ar_1$ is a 5- to 10-member mono- or bicyclic aromatic group, optionally substituted; where the —$NR_3R_4$ group is situated ortho to the NHC(=X) group; n=1 or 2; X=O or S; Y is O or S; and q=1 or 0. The invention also provides pharmaceutical compositions comprising compounds of formula I and/or salts, esters, and prodrugs thereof. These compounds modulate the activation and inactivation of potassium channels. The compounds are useful for the treatment and prevention of diseases and disorders—such as seizure disorders—which are affected by modulation of potassium ion channels.

20 Claims, No Drawings

U.S. PATENT DOCUMENTS

| | | | |
|---|---|---|---|
| 7,160,684 | B2 | 1/2007 | Argentieri et al. |
| 7,250,511 | B2 | 7/2007 | Bavetsias |
| 7,309,713 | B2 | 12/2007 | Rundfeldt et al. |
| 7,419,981 | B2 | 9/2008 | Field et al. |
| 2002/0013349 | A1 | 1/2002 | Wickenden |
| 2002/0015730 | A1 | 2/2002 | Hoffmann et al. |
| 2002/0183395 | A1 | 12/2002 | Argentieri |
| 2004/0198724 | A1 | 10/2004 | McNaughton-Smith et al. |
| 2005/0089473 | A1 | 4/2005 | Black et al. |
| 2005/0089559 | A1 | 4/2005 | Szelenyi |
| 2005/0090547 | A1 | 4/2005 | Szelenyi |
| 2005/0202394 | A1 | 9/2005 | Dobson |
| 2005/0277579 | A1 | 12/2005 | Krishnan et al. |
| 2007/0066612 | A1 | 3/2007 | Khanzhin et al. |

FOREIGN PATENT DOCUMENTS

| | | |
|---|---|---|
| DE | 3337593 | 10/1983 |
| DE | 3604575 A1 | 8/1986 |
| DE | 103 49 729.3 | 10/2003 |
| DE | 103 59 335 | 5/2005 |
| EP | 1 189 788 A1 | 8/1986 |
| EP | 0 343 429 | 5/1989 |
| EP | 1 334 972 | 8/2003 |
| EP | 1 407 768 | 4/2004 |
| EP | 1 813 285 A1 | 8/2007 |
| JP | 2000 143510 A | 5/2000 |
| RU | 2006117525 | 12/2005 |
| WO | WO 00/55137 | 9/2000 |
| WO | WO 00/59487 | 10/2000 |
| WO | WO 00/59508 | 10/2000 |
| WO | WO 01/01970 | 1/2001 |
| WO | WO 01/01972 | 1/2001 |
| WO | WO 01/09612 | 2/2001 |
| WO | WO 01/22953 | 4/2001 |
| WO | WO 02/080898 | 10/2002 |
| WO | WO 03/020706 | 3/2003 |
| WO | WO 03/097586 | 11/2003 |
| WO | WO 03/106454 | 12/2003 |
| WO | WO 2004/058739 | 7/2004 |
| WO | WO 2004/080950 | 9/2004 |
| WO | WO 2004/082677 | 9/2004 |
| WO | WO 2004/096767 | 11/2004 |
| WO | WO 2004/105795 | 12/2004 |
| WO | WO 2005/039576 | 5/2005 |
| WO | WO 2005/048975 | 6/2005 |
| WO | WO 2005/087754 | 9/2005 |
| WO | WO 2005/100349 | 10/2005 |
| WO | WO 2006/029623 | 3/2006 |
| WO | WO 2006/092143 | 9/2006 |
| WO | WO 2008/024398 | 2/2008 |
| WO | WO 2008/066900 | 6/2008 |

OTHER PUBLICATIONS

Beck et al., "Kreuzschmerzen in der Gynaekologischen praxis," Ginaekologe, Springer Verlag, Berlin German 2002 35(5):490-494.

Beeby et al. "The synthesis and properties of 2:7-Disubstituted 1:2:3:4-tetrahydroisoquinolines," *J. Chem. Soc.* 385:1799-1803 (1949).

Bialer et al., "Progress report on new antiepileptic drugs: a summary of the fourth Eilat conference (EILAT IV)," *Epilepsy Res.* 34:1-41 (1999).

Bialer, "Progress report on new antiepileptic drugs: a summary of the Sixth Eilat Conference (EILAT VI)," *Epilepsy Res.* 51:31-71 (2002).

Bialer, "Progress report on new antiepileptic drugs: a summary of the Seventh Eilat Conference (EILAT VII)," *Epilepsy Res.* 61:1-48 (2004).

Biervert et al., "A potassium channel mutation in neonatal human epilepsy," *Science* 279:403-406 (1998).

Blackburn-Munro and Jensen, "The anticonvulsant retigabine attenuates nociceptive behaviours in rat models of persistent and neuropathic pain," *Eur J Pharmacol.* 460: 109-116 (2003).

Brown and Adams, "Muscarinic suppression of a novel voltage-sensitive $K^+$ current in a vertebrate neurone," *Nature* 283:673-676 (1980).

Brown, D.A., *Ion Channels*, T. Narahashi, Ed. (Plenum Press, New York) pp. 55-94 (1988).

Charlier et al., "A pore mutation in a novel KQT-like potassium channel gene in an idiopathic epilepsy family," *Nat Genet.* 18:53-55 (1998).

Cooper et al., "Colocalization and coassembly of two human brain M-type potassium channel subunits that are mutated in epilepsy." *Proc. Natl. Acad. Sci. U.S.A.* 97:4914-4919 (2000).

Delmas and Brown, "Pathways modulating neural KCNQ/M (Kv7) potassium channels," *Nat. Rev. Neurosci.* 6:850-862 (2005).

Dickenson al., "Neurobiology of neuropathic pain: mode of action of anticonvulsants," *Eur. J. Pain* 6:51-60 (2002).

Dost et al., "The anticonvulsant retigabine potently suppresses epileptiform discharges in the low Ca++ and low Mg++ model in the hippocampal slice preparation," *Epilepsy Res.* 38:53-56 (2000).

Friedel and Fitton, "Flupirtine: a review of its analgesic properties, and therapeutic efficacy in pain states," *Drugs* 45:548-569 (1993).

Hiller et al., "Retigabine N-glucuronidation and its potential role in enterohepatic circulation," *Drug Metab. Dispos.* 27(5):605-612 (1999).

Hunt and Mantyh, "The molecular dynamics of pain control," *Nat. Rev. Neurosci.* 2:83-91 (2001).

Jentsch, "Neuronal KCNQ potassium channels; physiology and role in disease," *Nat. Rev. Neurosci.* 1:21-30 (2000).

Jiang et al., "X-ray structure of a voltage-dependent K+ channel," *Nature* 423:33-41 (2003).

Kharkovets et al., "Mice with altered KCNQ4 $K^+$ channels implicate sensory outer hair cells in human progressive deafness," *EMBO J.* 25:642-652 (2006).

Kibbe *Handbook of Pharmaceutical Excipients* (Pharmaceutical Press, London) (2000).

Kubisch et al., "KCNQ4, a novel potassium channel expressed in sensory outer hair cells, is mutated in dominant deafness," *Cell* 96:437-446 (1999).

Kuo et al., "Inhibition of $Na^+$ current by diphenhydramine and other diphenyl compounds: molecular determinants of selective binding to the inactivated channels" *Mol. Pharmacol.* 57(1):135-143(2000).

Lamas et al., "Effects of a cognition-enhancer, linopirdine (DuP 996), on M-type potassium currents ($I_{K(M)}$) and some other voltage- and ligand-gated membrane currents in rat sympathetic neurons," *Eur. J. Neurosci.* 9:605-616 (1997).

Lee et al., "Structure of the KvAP voltage-dependent $K^+$ channel and its dependence on the lipid membrane," *Proc. Natl. Acad. Sci. U.S.A.* 102:15441-15446 (2005).

Long et al., "Crystal Structure of a mammalian voltage-dependent *Shaker* family $K^+$ channel," *Science* 309:897-903 (2005).

Main et al., "Modulation of KCNQ2/3 potassium channels by the novel anticonvulsant retigabine," *Mol. Pharmacol.* 58:253-262 (2000).

Marrion, "Control of M-currents," *Annu. Rev. Physiol.* 59:483-504 (1997).

Parcej and Eckhardt-Strelau, Structural characterization of neuronal voltage-sensitive $K^+$ channels heterologously expressed in *Pichia pastoris, J.Mol. Biol.* 333:103-116 (2003).

Passmore et al., "KCNQ/M currents in sensory neurons: significance for pain therapy," *J. Neurosci.* 23:7227-7236 (2003).

Patani, "Bioisosterism: A Rational Approach in Drug Design" *Chem. Rev.* 96:3147-3176 (1996).

Porter et al., "Retigabine," *Neurotherapeutics* 4:149-154 (2007).

Reich et al., "Design and synthesis of novel 6,7-imidazotetrahydroquinoline inhibitors of thymidylate synthase using iterative protein crystal structure analysis," *J. Med. Chem.* 35:847-858 (1992).

Rogawski, MA, "KCNQ2/KCNQ3 K+ channels and the molecular pathogenesis of epilepsy: implications for therapy," *Trends Neurosci.* 23:393-398 (2000).

Rostock et al., "A new anticonvulsant with broad spectrum activity in animal models of epileptic seizures," *Epilepsy Res.*23:211-223 (1996).

Rundfeldt et al., "Multiple actions of the new anticonvulsant D-23129 on voltage-gated inward currents and GABA-induced currents in cultured neuronal cells (abstract)," *Naunyn-Schmiedeberg's Arch Pharmacol* 351 (Suppl):R160 (1995).

Rundfeldt, "Characterization of the K+ channel opening effect of the anti-convulsant retigabine in PC12 cells," *Epilepsy Res.* 35:99-107 (1999).

Rundfeldt, "The new anticonvulsant retigabine (D23129) acts as an opener of K+ channels in neuronal cells," *Eur. J. Pharmacol.* 336:243-249 (1997).

Schroeder et al., "KCNQ5, a novel potassium channel broadly expressed in brain, mediates M-type currents," *J. Biol. Chem.* 275:24089-24095 (2000).

Schroeder, "Moderate loss of function of cyclic-AMP-modulated KNCQ2/KCNQ3 K+ channels causes epilepsy," *Nature* 396:687-690 (1998).

Singh et al., "A novel potassium channel gene, KCNQ2, is mutated in an inherited epilepsy of newborns," *Nat Genet.* 18:25-29 (1998).

Suzuki and Dickenson, "Neuropathic pain: nerves bursting with excitement," *NeuroReport* 11:R17-R21 (2000).

Tatulian and Brown, "Effect of the KCNQ potassium channel opener retigabine on single KCNQ2/3 channels express in CHO cells," *J. Physiol.* 549:57-63 (2003).

Tatulian et al., "Activation of expressed KCNQ potassium currents and native neuronal M-type potassium currents by the anti-convulsant drug retigabine," *J. Neurosci.* 21:5535-5545 (2001).

Tober et al., "D-23129: a potent anticonvulsant in the amygdala kindling model of complex partial seizures," *Eur. J. Pharmacol.* 303:163-169 (1996).

Touboul et al. "A Comparative evaluation of the effects of Propafenone and lidocaine on early ventricular arrhythmias after acute myocardial infarction," *Eur. Heart J.* 9:1188-1193 (1988). Abstract.

Vippagunta et al., "Crystalline solids" *Adv. Drug Deliv. Rev.* 48:3-26 (2001).

Von Bebenburg et al., "Substituierte Polyaminopyridine" *Chemiker-Zeitung* 103:387-399 (1979). (German language article attached.).

Wang et al., "Positional cloning of a novel potassium channel gene: KVLQT1 mutations cause cardiac arrhythmias," *Nat Genet* 12:17-23 (1996).

Wang et al., "KCNQ2 and KCNQ3 potassium channel subunits: molecular correlates of the M-channel," *Science* 282:1890-1893 (1998).

Watanbe et al., "Disruption of the epilepsy KCNQ2 gene results in neural hyperexcitability," *J. Neurochem.* 75:28-33 (2000).

West, *Solid State Chemistry and Its Applications* (John Wiley & Sons, New York) pp. 358 and 365 (1988).

Wickenden et al., "KCNQ potassium channels: drug targets for the treatment of epilepsy and pain," *Exp. Opin. Thera. Patents* 14(4): 457-469 (2004).

Wickenden et al., "Retigabine, a novel anti-convulsant, enhances activation of KCNQ2/Q3 potassium channels," *Mol. Pharmacol.* 58:591-600 (2000).

Wolf (ed.), Burger's Medicinal Chemistry and Drug Discovery, 5th Edition vol. 1: Principles and Practice, John Wiley & Sons, New York, pp. 975-977 (1995).

Wu et al., "Regulatory perspectives of Type II prodrug development and time-dependent toxicity management: nonclinical Pharm/Tox analysis and the role of comparative toxicology" *Toxicology* 236:1-6 (2007).

Wuttke, "The new anticonvulsant retigabine favors voltage-dependent opening of the Kv7.2 (KCNQ2) channel by binding to its activation gate," *Mol. Pharmacol.* 67:1009-1017 (2005).

Zani et al., "Sodium channels are required during in vivo sodium chloride hyperosmolarity to stimulate increase in intestinal endothelial nitric oxide production" *Am. J. Physiol. Heart Circ. Physiol.* 288:H89-H95 (2005).

SUBSTITUTED ARYLAMINO-1,2,3,4-TETRAHYDRO NAPHTHALENES AND -2,3-DIHYDRO-1H-INDENES AS POTASSIUM CHANNEL MODULATORS

CROSS-REFERENCE TO RELATED APPLICATIONS

The present application is a divisional application of U.S. application Ser. No. 11/810,114 filed Jun. 4, 2007, now U.S. Pat. No. 7,960,436, which in turn claims benefit of U.S. Provisional Application No. 60/811,463 filed on Jun. 5, 2006.

FIELD OF THE INVENTION

The invention concerns novel compounds that modulate potassium ion channels. The compounds are useful for the treatment and prevention of diseases and disorders which are affected by regulation of potassium ion channels. One such malady is seizure disorders.

BACKGROUND OF THE INVENTION

Retigabine (N-[2-amino-4-(4-fluorobenzylamino)phenyl] carbamic acid, ethyl ester] (U.S. Pat. No. 5,384,330) has been found to be an effective treatment of seizure disorders in children. Bialer, M., et al., *Epilepsy Research* 1999, 34, 1-41. Retigabine has also been found to be useful in treating pain, including neuropathic pain. Blackburn-Munro and Jensen, *Eur. J. Pharmacol.* 2003, 460, 109-116.

"Benign familial neonatal convulsions" have been associated with mutations in the KCNQ2/3 channels. Biervert, C., et al., *Science* 1998, 27, 403-06; Singh, N. A., et al., *Nat. Genet.* 1998, 18, 25-29; Charlier, C., et al., *Nat. Genet.* 1998, 18, 53-55, Rogawski, *Trends in Neurosciences* 2000, 23, 393-398. Subsequent investigations have established that the major site of action of retigabine is the KCNQ2/3 channel. Wickenden, A. D. et al., *Mol. Pharmacol.* 2000, 58, 591-600; Main, M. J., et al., *Mol. Pharmcol.* 2000, 58, 253-62. Retigabine has been shown to increase the conductance of the channels at the resting membrane potential and to bind the activation gate of the KCNQ 2/3 channel. Wuttke, T. V., et al., *Mol. Pharmacol.* 2005, 67, 1009-1017.

The recognition of the site of action of retigabine has prompted a search for other potassium channel modulators among compounds structurally related to retigabine. Several such searches have been reported in the patent literature, most notably the following: WO 2004/058739; WO 2004/80950; WO 2004/82677; WO 2004/96767; WO 2005/087754; and WO 2006/029623.

DETAILED DESCRIPTION OF THE INVENTION

The invention provides compounds of formula I,

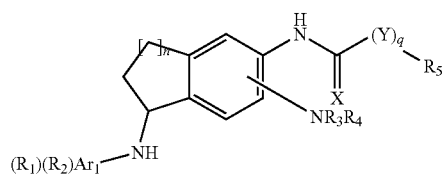

where $Ar_1$ is a 5- to 10-member mono- or bicyclic aromatic group, optionally containing 1-4 heteroatoms selected independently from N, O, and S; $R_1$ and $R_2$ are selected, independently, from H, CN, halogen, $CH_2CN$, OH, $NO_2$, $CH_2F$, $CHF_2$, $CF_3$, $CF_2CF_3$, $C_1$-$C_6$ alkyl, $OR_8$, $C(=O)R_9$, $C(=O)$ $OR_{10}$, $OC(=O)R_{11}$, $SR_{12}$, $NR_{13}C(=O)R_{14}$, $C(=O)$ $NR_{15}R_{16}$, $CH_2C(=O)NR_{15}R_{16}$, $NR_{17}R_{18}$, $SO_2R_{19}$, $N(R_{20})$ $SO_2R_{21}$, $SO_2NR_{22}R_{23}$, $C_3$-$C_6$ cycloalkyl, $CH_2C_3$-$C_6$ cycloalkyl, $C_5$-$C_6$ cycloalkenyl, $C_2$-$C_6$ alkenyl, or $C_2$-$C_6$ alkynyl; where the —$NR_3R_4$ group is situated ortho to the NHC(=X) group and $R_3$ and $R_4$ are, independently, H or $C_{1-6}$ alkyl, which $C_{1-6}$ alkyl group is optionally substituted with 1 or 2 groups selected, independently, from methyl, halogen, methoxy, and hydroxy, or $R_3$ and $R_4$ together form a 5- or 6-membered ring, optionally substituted with halogen, methyl, methoxy, or hydroxy and optionally containing one or two double bonds; n=1 or 2; X is O or S; Y is O or S; q=1 or 0; $R_5$ is $C_1$-$C_6$ alkyl, $(CHR_6)_w C_3$-$C_6$ cycloalkyl, $(CHR_6)_w CH_2 C_3$-$C_6$ cycloalkyl, $CH_2(CHR_6)_w C_3$-$C_6$ cycloalkyl, $(CHR_6)_w C_5$-$C_6$ cycloalkenyl, $CH_2(CHR_6)_w C_5$-$C_6$ cycloalkenyl, $C_2$-$C_6$ alkenyl, $C_2$-$C_6$ alkynyl, $Ar_2$, $(CHR_6)_w Ar_2$, $CH_2(CHR_6)_w Ar_2$, or $(CHR_6)_w CH_2 Ar_2$, where w=0-3, $Ar_2$ is a 5- to 10-member mono- or bicyclic aromatic group, optionally containing 1-4 ring heteroatoms selected independently from N, O, and S; $R_6$ is $C_1$-$C_3$ alkyl; and $R_8$-$R_{23}$ are, independently, H, $C_1$-$C_6$ alkyl, $C_3$-$C_6$ cycloalkyl, $(CHR_6)_w C_3$-$C_6$ cycloalkyl, $C_2$-$C_6$ alkenyl, $C_2$-$C_6$ alkynyl, where all alkyl, cycloalkyl, alkenyl, alkynyl, aryl, groups are optionally substituted with one or two substituents selected independently from $C_1$-$C_3$ alkyl, halogen, OH, OMe, CN, $CH_2F$, and trifluoromethyl; where, additionally, the alkenyl and alkynyl groups are optionally substituted with phenyl or $C_3$-$C_6$ cycloalkyl; and where all cycloalkyl groups optionally contain one or two ring heteroatoms selected independently from N, O, and S. Such compounds are potassium channel modulators. By "modulators" is meant potassium channel openers or activators at the resting membrane potential, but inhibitors for peak current at the positive voltage range of action potential.

In one generic embodiment, the invention provides or contemplates a compound of formula I, where NH—C(=X)—$(Y)_q$—$R_5$ is NHC(=O)$R_5$.

In another generic embodiment, the invention provides or contemplates a compound of formula I, where NH—C(=X)—$(Y)_q$—$R_5$ is NHC(=O)O$R_5$.

In another generic embodiment, the invention provides or contemplates a compound of formula I, where NH—C(=X)—$(Y)_q$—$R_5$ is NHC(=S)S$R_5$.

In another generic embodiment, the invention provides or contemplates a compound of formula I, where NH—C(=X)—$(Y)_q$—$R_5$ is NHC(=S)$R_5$.

In another generic embodiment, the invention provides or contemplates a compound of formula I, where NH—C(=X)—$(Y)_q$—$R_5$ is NHC(=S)O$R_5$.

In another generic embodiment, the invention provides or contemplates a compound of formula I, where NH—C(=X)—$(Y)_q$—$R_5$ is NHC(=O)S$R_5$.

In one subgeneric embodiment, the invention provides compounds of formula IA,

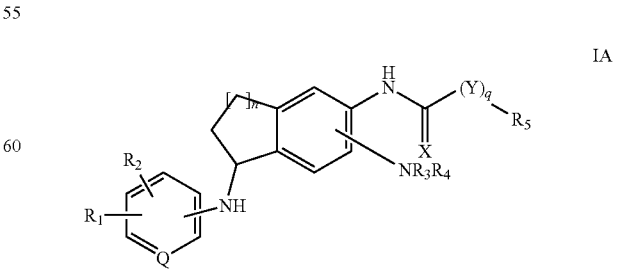

where Q=$CR_7$ or N, where $R_7$ is H or $C_1$-$C_6$ alkyl.

In another subgeneric embodiment, the invention provides or contemplates a compound of formula IB,

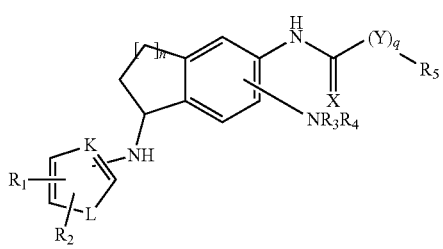

where L is O, S, or NH, and K is N or CH.

In another subgeneric embodiment, the invention provides or contemplates a compound of formula IC-1 or IC-2,

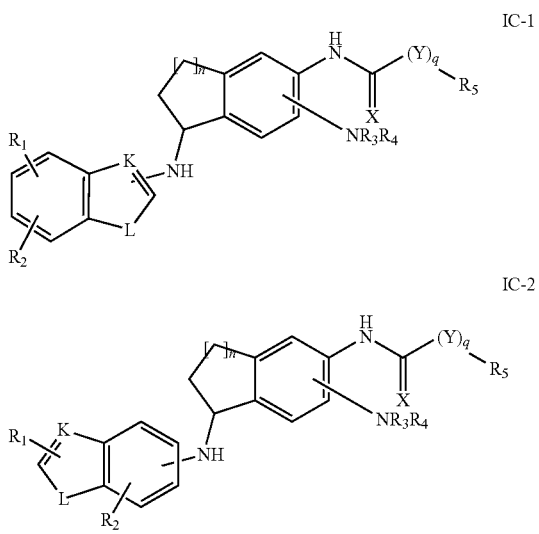

where L is O, S, or NH, and K is N or CH.

In another subgeneric embodiment, the invention provides or contemplates a compound of formula ID-1 or ID-2,

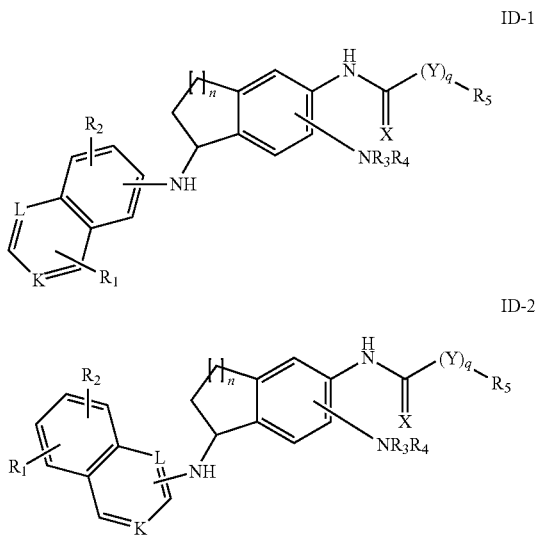

where K and L are, independently, N or CH.

In a more specific subgeneric embodiment, the invention provides or contemplates compounds of formula IA, where NH—C(=X)—(Y)$_q$—R$_5$ is NHC(=O)R$_5$ or NHC(=O)OR$_5$.

In another more specific subgeneric embodiment, the invention provides or contemplates compounds of formula IA, where NH—C(=X)—(Y)$_q$—R$_5$ is NHC(=S)R$_5$ or NHC(=S)SR$_5$.

In another more specific subgeneric embodiment, the invention provides or contemplates compounds of formula IA, where NH—C(=X)—(Y)$_q$—R$_5$ is NHC(=S)OR$_5$ or NHC(=O)SR$_5$.

In another more specific subgeneric embodiment, the invention provides or contemplates compounds of formula IB, where NH—C(=X)—(Y)$_q$—R$_5$ is NHC(=O)R$_5$ or NHC(=O)OR$_5$.

In another more specific subgeneric embodiment, the invention provides or contemplates compounds of formula IB, where NH—C(=X)—(Y)$_q$—R$_5$ is NHC(=S)R$_5$ or NHC(=S)SR$_5$.

In another more specific subgeneric embodiment, the invention provides or contemplates compounds of formula IB, where NH—C(=X)—(Y)$_q$—R$_5$ is NHC(=S)OR$_5$ or NHC(=O)SR$_5$.

In another more specific subgeneric embodiment, the invention provides or contemplates compounds of formula IC-1 or IC-2, where NH—C(=X)—(Y)$_q$—R$_5$ is NHC(=O)R$_5$ or NHC(=O)OR$_5$.

In another more specific subgeneric embodiment, the invention provides or contemplates compounds of formula IC-1 or IC-2, where NH—C(=X)—(Y)$_q$—R$_5$ is NHC(=S)R$_5$ or NHC(=S)SR$_5$.

In another more specific subgeneric embodiment, the invention provides or contemplates compounds of formula IC-1 or IC-2, where NH—C(=X)—(Y)$_9$—R$_5$ is NHC(=S)OR$_5$ or NHC(=O)SR$_5$.

In another more specific subgeneric embodiment, the invention provides or contemplates compounds of formula ID-1 or ID-2, where NH—C(=X)—(Y)$_q$—R$_5$ is NHC(=O)R$_5$ or NHC(=O)OR$_5$.

In another more specific subgeneric embodiment, the invention provides or contemplates compounds of formula ID-1 or ID-2, where NH—C(=X)—(Y)$_q$—R$_5$ is NHC(=S)R$_5$ or NHC(=S)SR$_5$.

In another more specific subgeneric embodiment, the invention provides or contemplates compounds of formula ID-1 or ID-2, where NH—C(=X)—(Y)$_q$—R$_5$ is NHC(=S)OR$_5$ or NHC(=O)SR$_5$.

In a more specific subgeneric embodiment, the invention provides compounds of formula IA, where NH—C(=X)—(Y)$_q$—R$_5$ is NHC(=O)—C$_1$-C$_6$ alkyl, NHC(=O)—OC$_1$-C$_6$ alkyl, NHC(=O)—(CH$_2$)$_2$C$_5$-C$_6$ cycloalkyl, or NHC(=O)O)—(CH$_2$)$_2$C$_5$-C$_6$ cycloalkyl.

In another specific subgeneric embodiment, the invention provides compounds of formula IA according to the structure below

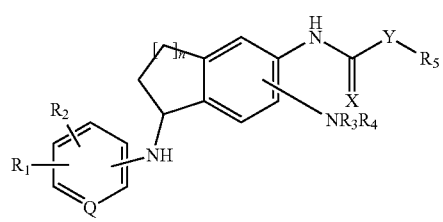

In another specific subgeneric embodiment, the invention provides compounds of formula IA according to the structure below

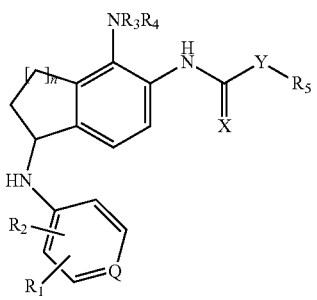

In another more specific subgeneric embodiment, the invention provides compounds of formula IA according to the structure below

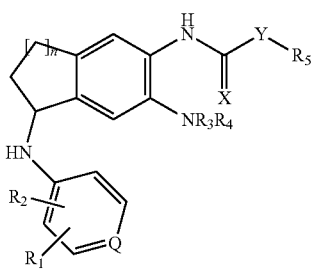

In another more specific subgeneric embodiment, the invention provides compounds of formula IA according to the structure below

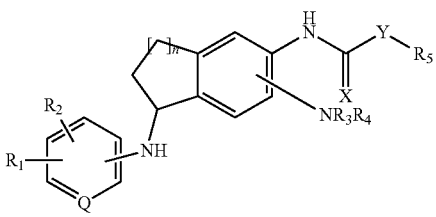

In another more specific subgeneric embodiment, the invention provides compounds of formula IA according to the structure below

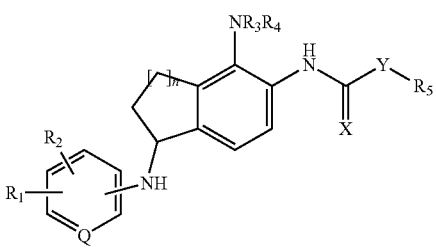

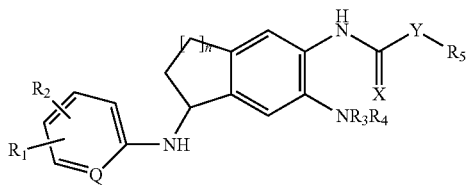

In another more specific subgeneric embodiment, the invention provides compounds of formula IA according to the structure below

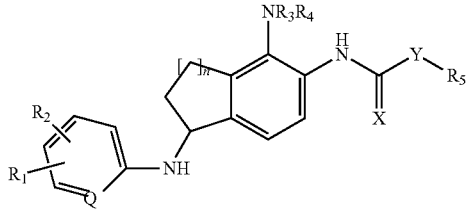

In another more specific subgeneric embodiment, the invention provides compounds of formula IA according to the structure below

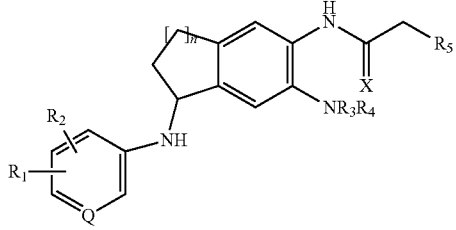

In another more specific subgeneric embodiment, the invention provides compounds of formula IA according to the structure below

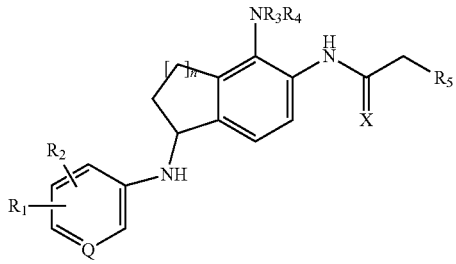

In another more specific subgeneric embodiment, the invention provides compounds of formula IA according to the structure below

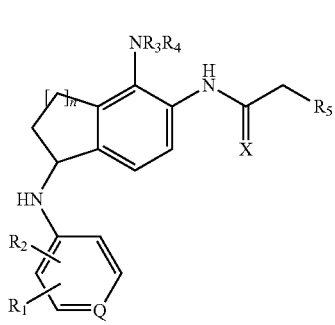

In another more specific subgeneric embodiment, the invention provides compounds of formula IA according to the structure below

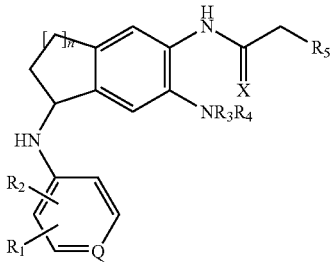

In another more specific subgeneric embodiment, the invention provides compounds of formula IA according to the structure below

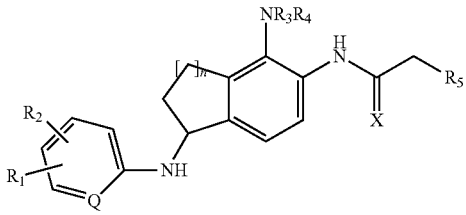

In another more specific subgeneric embodiment, the invention provides compounds of formula IA according to the structure below

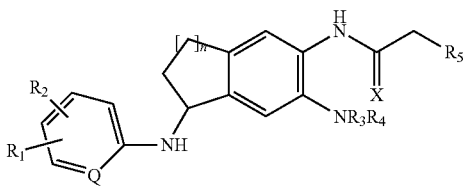

In additional more specific subgeneric embodiments, the invention provides compounds of formula IA as shown below

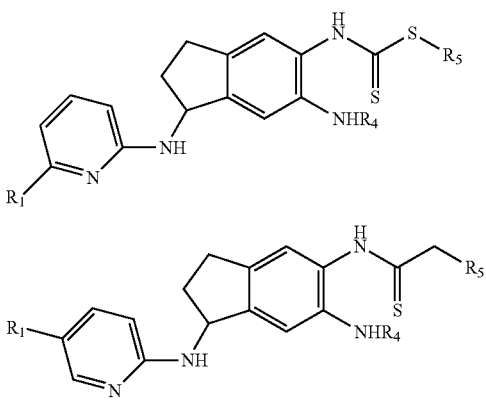

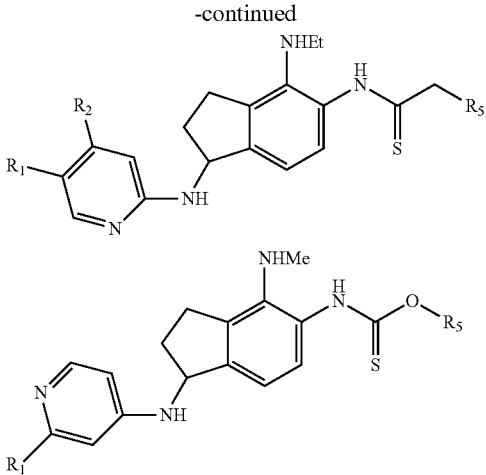

In another subgeneric embodiment, the invention provides a compound of formula IC-2 as shown below

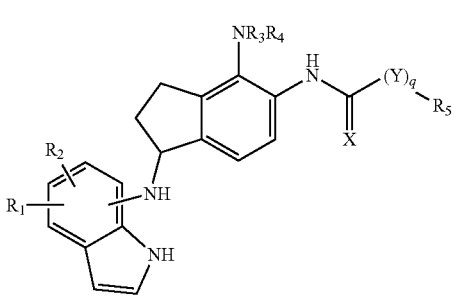

In another subgeneric embodiment, the invention provides a compound as shown below

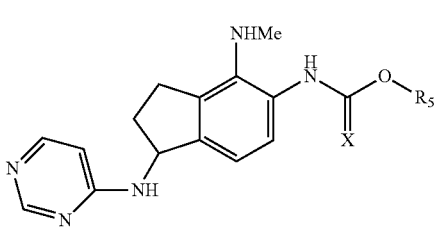

In another subgeneric embodiment, the invention provides a compound of formula IC-2 as shown below

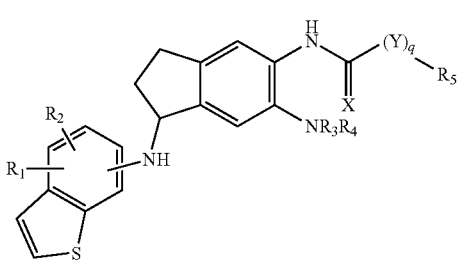

In still more specific subgeneric embodiments, the invention provides compounds where Ar₁ is phenyl, as shown below

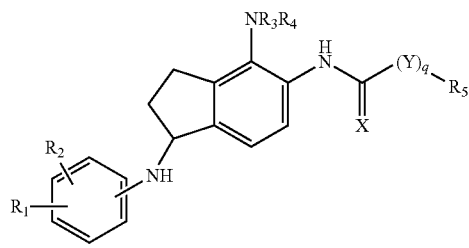

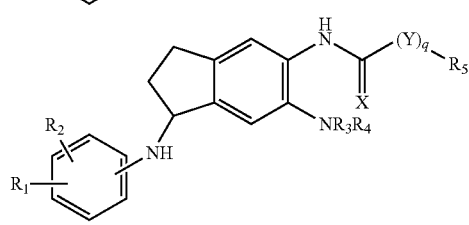

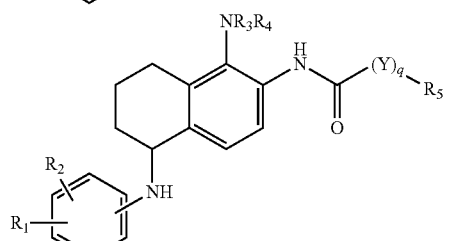

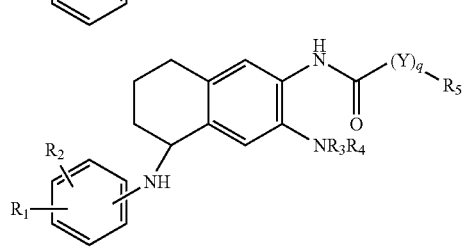

In additional still more specific subgeneric embodiments, the invention provides compounds where Ar₁ is quinolyl, as shown below

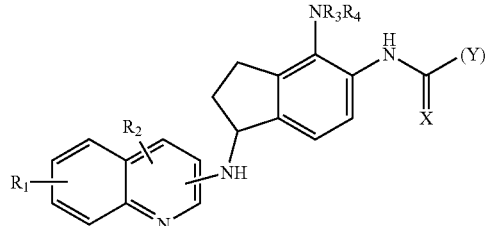

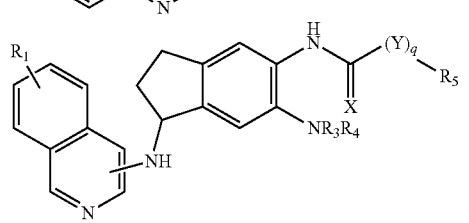

In additional more specific subgeneric embodiments, the invention provides compounds where Ar₁ is pyridyl, as shown below

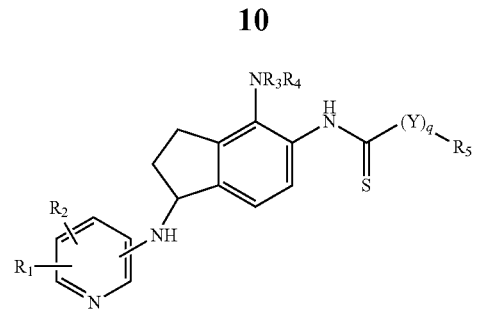

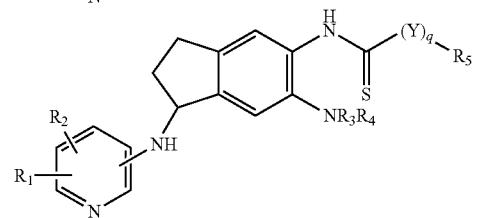

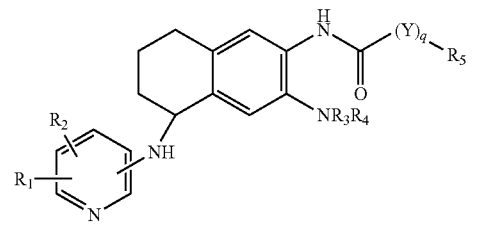

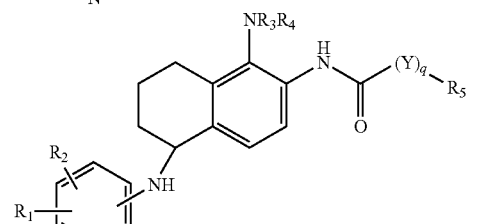

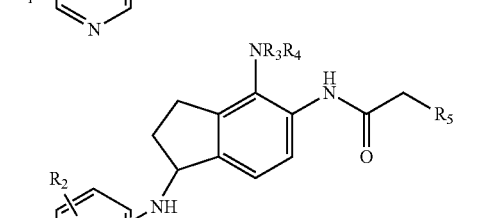

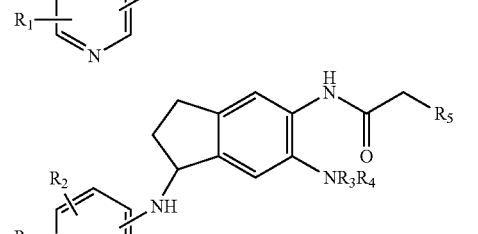

In additional, more specific subgeneric embodiments, the invention provides compounds as shown below

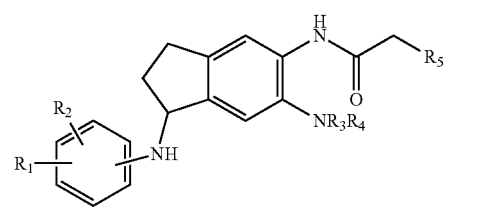

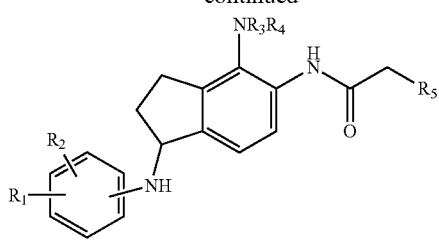

In additional, more specific subgeneric embodiments, the invention provides compounds as shown below

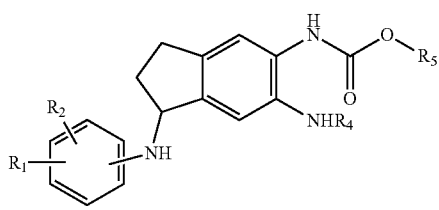

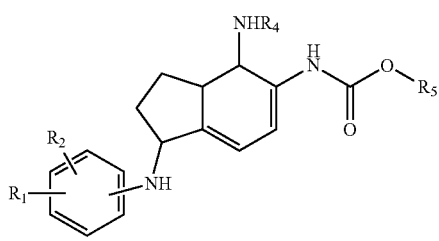

In yet additional more specific subgeneric embodiments, the invention provides compounds as shown below

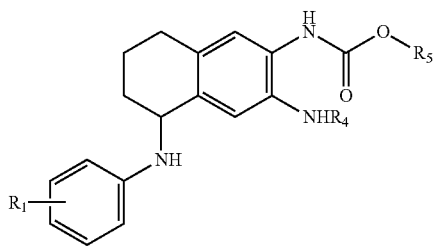

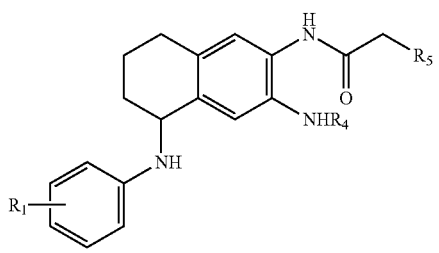

In more specific subgeneric embodiments, the invention provides compounds as shown below

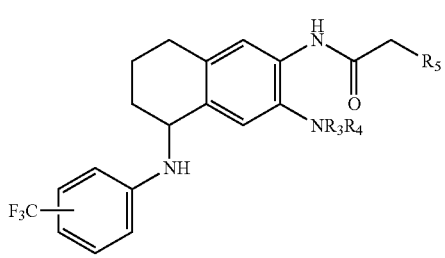

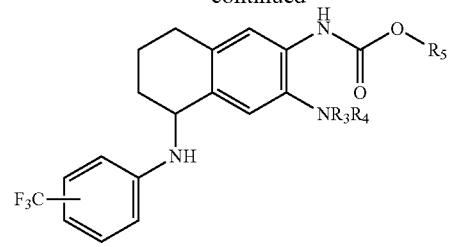

In additional more specific subgeneric embodiments, the invention provides compounds as shown below

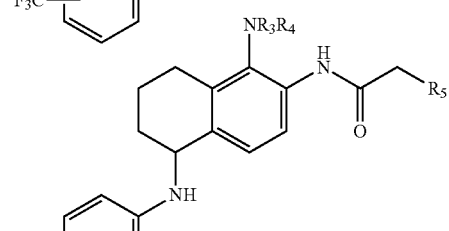

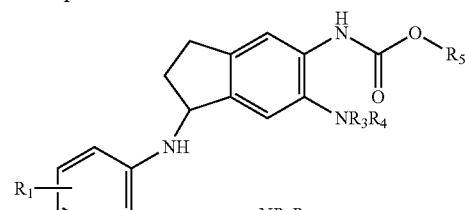

In additional subgeneric embodiments, the invention provides compounds as shown below

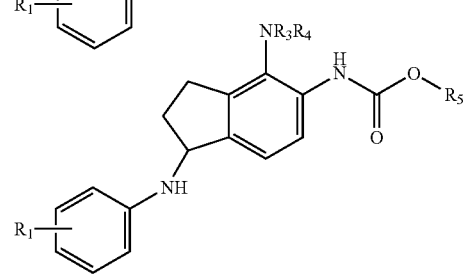

In additional subgeneric embodiments, the invention provides compounds as shown below

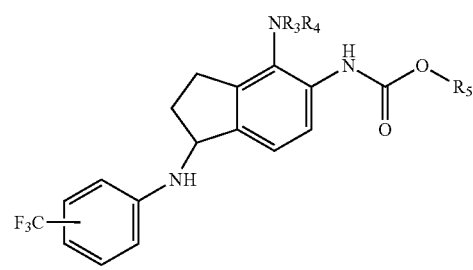

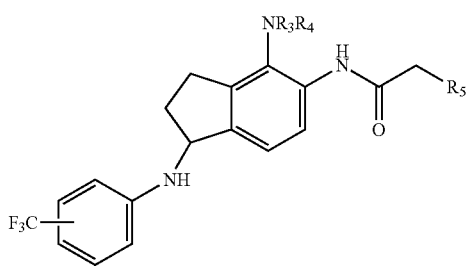

In additional subgeneric embodiments, the invention provides compounds as shown below

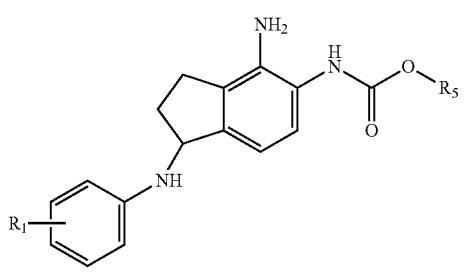

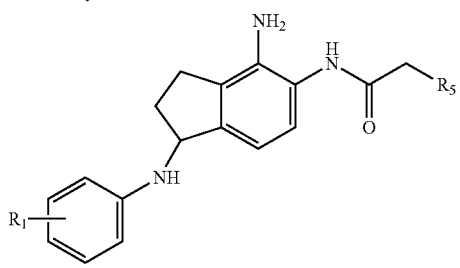

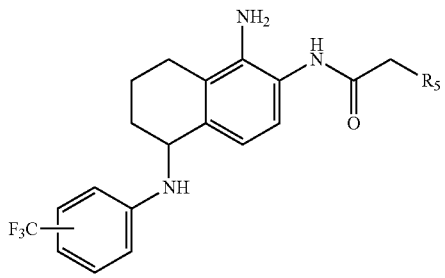

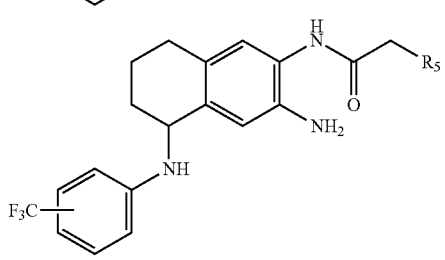

In another embodiment, this invention provides or contemplates a compound of formula IB, where $Ar_1$ is a 2- or 3-thienyl or furanyl or a compound of formula IC-1, where $Ar_1$ is benzothienyl, which group may be substituted. Subgeneric compounds of that type are shown below.

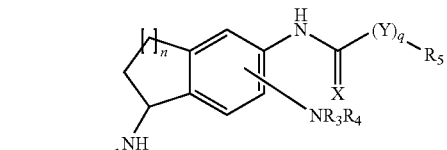

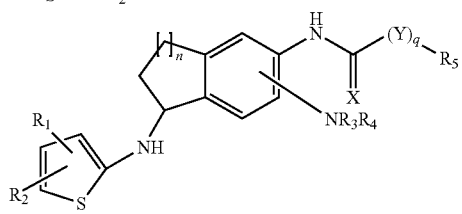

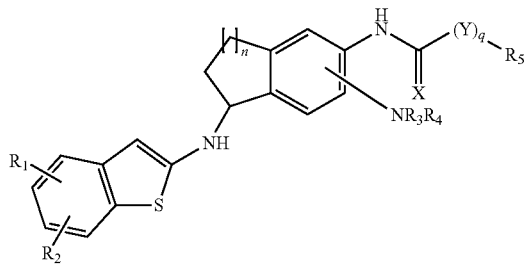

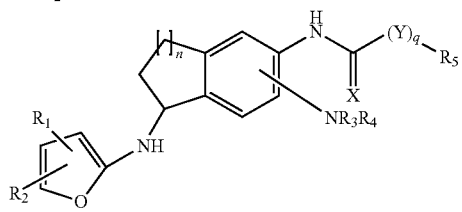

In additional embodiments, the invention provides compounds in which $Ar_1$ is pyrrole or indole, as shown below

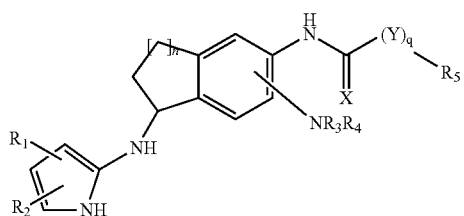

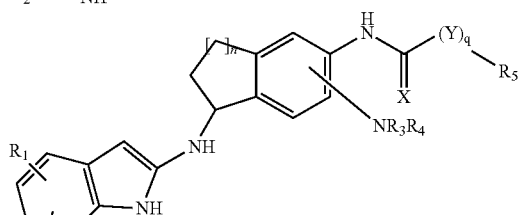

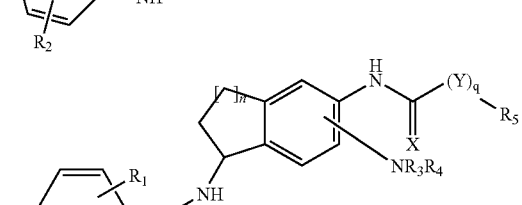

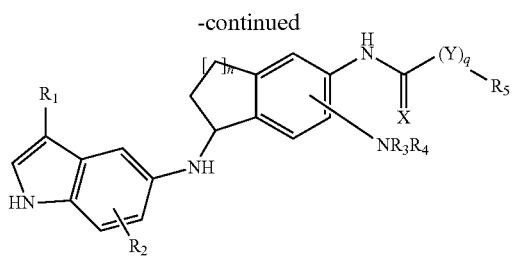

In additional subgeneric embodiments, the invention contemplates compounds in which $Ar_1$ is purine, as shown below

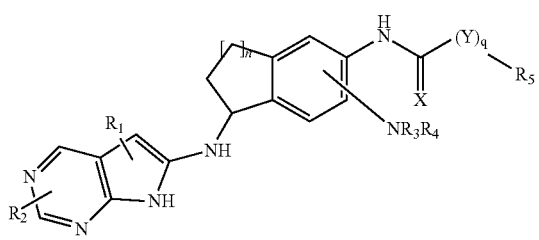

In additional subgeneric embodiments, the invention contemplates compounds as shown below

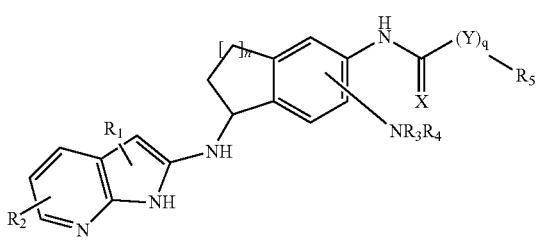

In a more specific embodiment, this invention provides a compound of formula I, where $Ar_1$ is phenyl or pyridyl, n is zero or 1, $R_1$ is CN, $CH_2CN$, or halogen, q is 1, and X and Y are both O.

In another more specific embodiment, this invention provides a compound of formula IA, formula IB, formula IC-1, or formula IC-2, where n is zero or 1, $R_1$ is F, $CH_2F$, $CHF_2$, $CF_3$, or $CF_2CF_3$, q is 1, and X and Y are both O.

In another more specific embodiment, this invention provides a compound of formula IA, or formula IB, or formula IC-1 or IC-2, where n is zero or 1, $R_1$ is $NHC_1$-$C_6$ alkyl or NHC(=O)$C_1$-$C_6$ alkyl, q is 1, and X and Y are both O.

In a more specific embodiment, this invention provides a compound of formula IA, or formula IB, or formula IC-1 or IC-2, where n is zero or 1, $R_1$ is C(=O)—NH—$C_1$-$C_6$ alkyl, $SO_2C_1$-$C_6$alkyl, $SO_2NHC_1$-$C_6$alkyl, q is 1, and X and Y are both O.

In a more specific embodiment, this invention provides a compound of formula IA, or formula IB, or formula IC-1 or IC-2, where n is zero or 1, $R_1$ is OH, OMe, OEt, SMe, or SEt, q is 1, and X and Y are both O.

In another more specific embodiment, this invention provides a compound of formula IA, or formula IB, or formula IC-1 or IC-2, where n is zero or 1, $R_1$ is vinyl, allyl, methylethynyl, or phenylethynyl.

In another more specific embodiment, this invention provides a compound of formula IA, or formula IB, or formula IC-1 or IC-2, where n is zero or 1, $R_1$ is C(=O)O$C_1$-$C_6$ alkyl or OC(=O)$C_1$-$C_6$ alkyl, q is 1, and X and Y are both O.

In a still more specific embodiment, this invention provides a compound of formula I, where $Ar_1$ is phenyl or pyridyl, n is zero or 1, $R_1$ is C(=O)—NH—$C_1$-$C_4$ alkyl, $SO_2C_1$-$C_4$alkyl, $SO_2NHC_1$-$C_4$ alkyl, q is 1, and X and Y are both O.

In a more specific embodiment, this invention provides a compound of formula I, where $Ar_1$ is phenyl or pyridyl, n is zero or 1, $R_1$ is OH, OMe, OEt, SMe, or SEt, q is 1, and X and Y are both O.

In another more specific embodiment, this invention provides a compound of formula I, where $Ar_1$ is phenyl or pyridyl, n is zero or 1, and $R_1$ is vinyl, allyl, methylethynyl, or phenylethynyl.

In another more specific embodiment, this invention provides a compound of formula I, where $Ar_1$ is phenyl or pyridyl, n is zero or 1, $R_1$ is C(=O)O$C_1$-$C_4$ alkyl or OC(=O)$C_1$-$C_4$alkyl, q is 1, and X and Y are both O.

In another more specific embodiment, this invention provides a compound of formula I, where $Ar_1$ is phenyl or pyridyl, $R_1$ is $C_2$-$C_6$ alkenyl or $C_2$-$C_6$ alkynyl, n is zero or 1, q is 1, and X and Y are both O.

In another more specific embodiment, this invention provides a compound of formula I, where $Ar_1$ is phenyl or pyridyl, $R_1$ is $C_1$-$C_4$ alkyl, n is zero or 1, q is 1, and X and Y are both O.

In another more specific embodiment, this invention provides a compound of formula I, where $Ar_1$ is phenyl or pyridyl, $R_1$ is $SC_1$-$C_6$ alkyl, n is zero or 1, q is 1, and X and Y are both O.

In another more specific embodiment, this invention provides a compound of formula I, where $Ar_1$ is monosubstituted phenyl, X is O, q is 1, and Y is S.

In another more specific embodiment, this invention provides a compound of formula I, where $Ar_1$ is monosubstituted phenyl, X is O, q is 1, and Y is O.

In another more specific embodiment, the invention provides a compound of formula I, where $Ar_1$ is monosubstituted phenyl, X is O, and q is zero.

In another more specific embodiment, this invention provides a compound of formula I, where $Ar_1$ is monosubstituted phenyl, X is S, q is 1, and Y is S.

In another more specific embodiment, this invention provides a compound of formula I, where $Ar_1$ is monosubstituted phenyl, X is S, q is 1, and Y is O.

In another more specific embodiment, the invention provides a compound of formula I, where $Ar_1$ is monosubstituted phenyl, X is S, and q is zero.

In a still more specific embodiment, this invention provides a compound of formula I, where $Ar_1$ is monosubstituted phenyl, $R_1$ is alkyl, monofluoroalkyl, difluoroalkyl, trifluoroalkyl, F, or Cl; $R_3$ and $R_4$ are both H; X is O; and q is zero.

In a still more specific embodiment, this invention provides a compound of formula I, where $Ar_1$ is monosubstituted phenyl, $R_1$ is alkyl, fluoroalkyl, or halo, $R_3$ and $R_4$ are H or methyl, X is O, q is 1, and Y is O.

In a more specific embodiment, this invention provides a compound of formula I, where $Ar_1$ is phenyl or pyridyl, $R_3$ and $R_4$ are H or methyl, n is zero or 1, $R_1$ is $C_1$-$C_6$ alkyl, q is 1, and X and Y are both O.

In a more specific embodiment, this invention provides a compound of formula I, where $Ar_1$ is phenyl or pyridyl, $R_3$ and $R_4$ are H or methyl, n is zero or 1, $R_1$ is CN, $CH_2CN$, or halogen, q is 1, and X and Y are both O.

In a more specific embodiment, this invention provides a compound of formula I, where $Ar_1$ is phenyl or pyridyl, n is zero or 1, $R_1$ is $CH_2F$, $CHF_2$, $CF_3$, or $CF_2CF_3$, q is 1, and X and Y are both O.

In a more specific embodiment, this invention provides a compound of formula I, where $Ar_1$ is phenyl or pyridyl, n is zero or 1, $R_1$ is $OC_1$-$C_6$ alkyl or $C(=O)C_1$-$C_6$ alkyl, q is 1, and X and Y are both O.

In a more specific embodiment, this invention provides a compound of formula I, where $Ar_1$ is phenyl or pyridyl, n is zero or 1, $R_1$ is $C(=O)OC_1$-$C_6$ alkyl or $OC(=O)C_1$-$C_6$ alkyl, q is 1, and X and Y are both O.

In a more specific embodiment, this invention provides a compound of formula I, where $Ar_1$ is phenyl or pyridyl, $R_1$ is $C_2$-$C_6$ alkenyl or $C_2$-$C_6$ alkynyl, n is zero or 1, q is 1, and X and Y are both O.

In a more specific embodiment, this invention provides a compound of formula I, where $Ar_1$ is phenyl or pyridyl, $R_1$ is $SC_1$-$C_6$ alkyl, n is zero or 1, q is 1, and X and Y are both O.

In a more specific embodiment, this invention provides a compound of formula I, where $Ar_1$ is phenyl or pyridyl, $R_3$ and $R_4$ are H or methyl, n is zero or 1, $R_1$ is $C_1$-$C_6$ alkyl, q is zero, and X is O.

In a more specific embodiment, this invention provides a compound of formula I, where $Ar_1$ is phenyl or pyridyl, $R_3$ and $R_4$ are H or methyl, n is zero or 1, $R_1$ is CN, $CH_2CN$, or halogen, q is zero, and X is O.

In a more specific embodiment, this invention provides a compound of formula I, where $Ar_1$ is phenyl or pyridyl, $R_3$ and $R_4$ are H or methyl, n is zero, $R_1$ is F, $CH_2F$, $CHF_2$, $CF_3$, or $CF_2CF_3$, q is 1, and X is O.

In a more specific embodiment, this invention provides a compound of formula I, where $Ar_1$ is phenyl or pyridyl, n is zero or 1, $R_1$ is $OC_1$-$C_6$ alkyl or $C(=O)C_1$-$C_6$ alkyl, q is 1, and X is O.

In a more specific embodiment, this invention provides a compound of formula I, where $Ar_1$ is phenyl or pyridyl, n is zero or 1, $R_1$ is $C(=O)OC_1$-$C_6$ alkyl or $OC(=O)C_1$-$C_6$ alkyl, q is 1, and X is O.

In a more specific embodiment, this invention provides a compound of formula I, where $Ar_1$ is phenyl or pyridyl, $R_1$ is $C_2$-$C_6$ alkenyl or $C_2$-$C_6$ alkynyl, n is zero or 1, q is 1, and X is O.

In a more specific embodiment, this invention provides a compound of formula I, where $Ar_1$ is phenyl or pyridyl, $R_1$ is $SC_1$-$C_6$ alkyl, n is zero or 1, q is 1, and X is O.

In a more specific embodiment, this invention provides a compound of formula I, where $Ar_1$ is phenyl or pyridyl, $R_3$ and $R_4$ are H or methyl, n is zero or 1, $R_1$ is $C_1$-$C_6$ alkyl, q is 1, and X is O.

In a more specific embodiment, this invention provides a compound of formula I, where $Ar_1$ is phenyl or pyridyl, $R_3$ and $R_4$ are H or methyl, n is zero or 1, $R_1$ is CN, $CH_2CN$, or halogen, q is 1, and X is O.

In a more specific embodiment, this invention provides a compound of formula I, where $Ar_1$ is phenyl or pyridyl, $R_3$ and $R_4$ are H or methyl, n is 1, $R_1$ is F, $CH_2F$, $CHF_2$, $CF_3$, or $CF_2CF_3$, q is 1, and X is O.

In a more specific embodiment, this invention provides a compound of formula I, where $Ar_1$ is phenyl or pyridyl, n is zero or 1, $R_1$ is $OC_1$-$C_6$ alkyl or $C(=O)C_1$-$C_6$ alkyl, q is 1, and X is O.

In a more specific embodiment, this invention provides a compound of formula I, where $Ar_1$ is phenyl or pyridyl, n is zero or 1, $R_1$ is $C(=O)OC_1$-$C_6$ alkyl or $OC(=O)C_1$-$C_6$ alkyl, q is 1, and X is O.

In a more specific embodiment, this invention provides a compound of formula I, where $Ar_1$ is phenyl or pyridyl, $R_1$ is $C_2$-$C_6$ alkenyl or $C_2$-$C_6$ alkynyl, n is zero or 1, q is 1, and X is O.

In a more specific embodiment, this invention provides a compound of formula I, where $Ar_1$ is phenyl or pyridyl, $R_1$ is $SC_1$-$C_6$ alkyl, n is zero or 1, q is 1, and X is O.

In another embodiment, this invention provides or contemplates a compound of formula I, in which $R_5$ is $C_1$-$C_6$ alkyl.

In another embodiment, this invention provides or contemplates a compound of formula I, in which $R_5$ is $(CHR_6)_w C_3$-$C_6$ cycloalkyl, where w is 1 or 2 and $R_6$ is H or methyl.

In another embodiment, this invention provides or contemplates a compound of formula I, in which $R_5$ is $(CHR_6)_w CH_2 C_3$-$C_6$ cycloalkyl, where w is 1 or 2 and $R_6$ is H or methyl.

In another embodiment, this invention provides or contemplates a compound of formula I, in which $R_5$ is $CH_2(CHR_6)_w C_3$-$C_6$ cycloalkyl, where w is 1 or 2 and $R_6$ is H or methyl.

In another embodiment, this invention provides or contemplates a compound of formula I, in which $R_5$ is $(CHR_6)_w C_5$-$C_6$ oxacycloalkyl, where w is 1 or 2 and $R_6$ is H or methyl.

In another embodiment, this invention provides or contemplates a compound of formula I, in which $R_5$ is $(CHR_6)_w C_5$-$C_6$ azacycloalkyl, where w is 1 or 2 and $R_6$ is H or methyl.

In another embodiment, this invention provides or contemplates a compound of formula I, in which $R_5$ is $(CHR_6)_w C_5$-$C_6$ thiacycloalkyl, where w is 1 or 2 and $R_6$ is H or methyl.

In another embodiment, this invention provides or contemplates a compound of formula I, in which $R_5$ is $(CHR_6)_w CH_2 C_5$-$C_6$ azacycloalkyl, where w is 1 or 2 and $R_6$ is H or methyl.

In another embodiment, this invention provides or contemplates a compound of formula I, in which $R_5$ is $CH_2(CHR_6)_w C_3$-$C_6$ azacycloalkyl, where w is 1 or 2 and $R_6$ is H or methyl.

In a more specific embodiment, this invention provides or contemplates a compound of formula I, in which $R_5$ is $(CHR_6)_w Z$, where w is 1 or 2, $R_6$ is H or methyl, and Z is piperidinyl.

In another more specific embodiment, this invention provides or contemplates a compound of formula I, in which $R_5$ is $(CHR_6)_w Z$, where w is 1 or 2, $R_6$ is H or methyl, and Z is 1-pyrrolidinyl or 1-piperidinyl.

In another more specific embodiment, this invention provides or contemplates a compound of formula I, in which $R_5$ is $(CHR_6)_w Z$, where w is 1 or 2, $R_6$ is H or methyl, and Z is 2-pyrrolidinyl or 3-pyrrolidinyl.

In another embodiment, this invention provides or contemplates a compound of formula I, in which $R_5$ is $(CHR_6)_w Z$, where w is 1 or 2, $R_6$ is H or methyl, and Z is morpholyl, thiazolidinyl, oxazolidinyl, isothiazolidinyl, or isoxazolidinyl.

In another embodiment, this invention provides or contemplates a compound of formula I, in which $R_5$ is $(CHR_6)_w CH_2 C_3$-$C_6$ cycloalkyl, where w is 1 or 2 and $R_6$ is H or methyl.

In another embodiment, this invention provides or contemplates a compound of formula I, in which $R_5$ is $CH_2(CHR_6)_w C_3$-$C_6$ cycloalkyl, where w is 1 or 2 and $R_6$ is H or methyl.

In another embodiment, this invention provides or contemplates a compound of formula I, in which $R_5$ is $(CHR_6)_w C_3$-$C_6$ cycloalkyl, where w is 1 or 2 and $R_6$ is H or methyl.

In a more specific embodiment, this invention provides or contemplates a compound of formula IA, in which $R_5$ is $(CH_2)_w$—$C_5$-$C_6$ cycloalkyl.

In another embodiment, this invention provides or contemplates a compound of formula I, in which $R_5$ is CH=CH—$C_3$-$C_6$ cycloalkyl, where the carbon-carbon double bond has the E configuration.

In another embodiment, this invention provides or contemplates a compound of formula I, in which $R_5$ is CH=CH—$C_3$-$C_6$ cycloalkyl, where the carbon-carbon double bond has the Z configuration.

In another embodiment, this invention provides or contemplates a compound of formula I, in which $R_5$ is $CH_2$—

CH=CH—C$_3$-C$_6$ cycloalkyl, where the carbon-carbon double bond has the E configuration.

In another embodiment, this invention provides or contemplates a compound of formula I, in which R$_5$ is CH$_2$CH=CH—C$_3$-C$_6$ cycloalkyl, where the carbon-carbon double bond has the Z configuration.

In another embodiment, this invention provides or contemplates a compound of formula I, in which R$_5$ is CH=CH—CH$_2$—C$_3$-C$_6$ cycloalkyl, where the carbon-carbon double bond has the E configuration.

In another embodiment, this invention provides or contemplates a compound of formula I, in which R$_5$ is CH=CH—CH$_2$—C$_3$-C$_6$ cycloalkyl, where the carbon-carbon double bond has the Z configuration.

In another, more specific embodiment, this invention provides or contemplates a compound of formula I, in which R$_5$ is (CHR$_6$)$_w$C$_3$-C$_6$ cycloalkyl, where the cycloalkyl group is monosubstituted.

In another embodiment, this invention provides or contemplates a compound of formula I, in which R$_5$ is CH=CH—CH$_2$—C$_3$-C$_6$ cycloalkyl or CH=CH—C$_3$-C$_6$ cycloalkyl, where the cycloalkyl group is monosubstituted.

In another embodiment, this invention provides a compound of formula IA, in which R$_3$ and R$_4$ are H or methyl, n is 1, q is 1, X is O and R$_5$ is C$_5$-C$_6$ alkyl.

Illustrative examples of contemplated compounds of this invention are provided below. These are provided in order to indicate that a broad range of compounds and substitution patterns is contemplated. This group of examples should not be construed as limiting the scope of this invention.

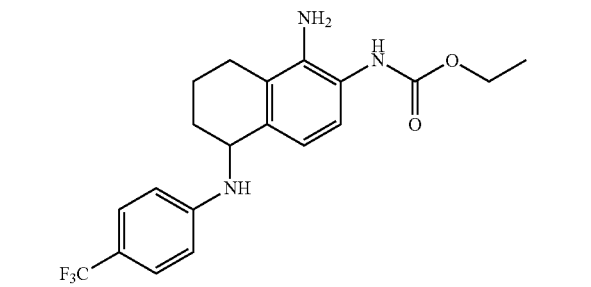

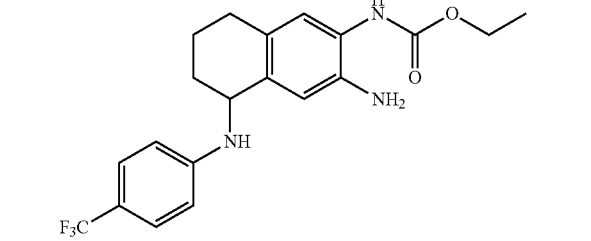

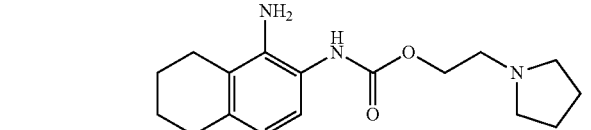

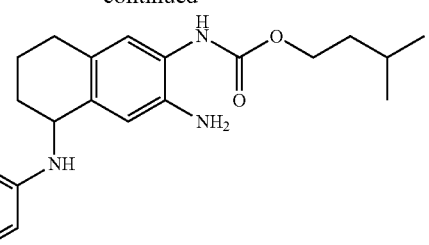

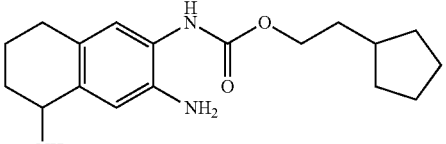

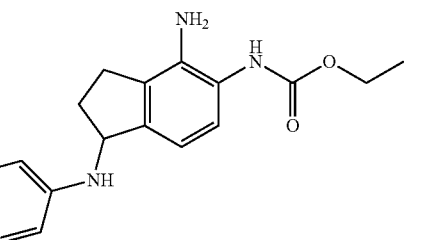

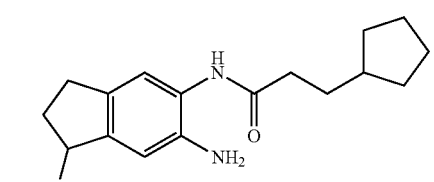

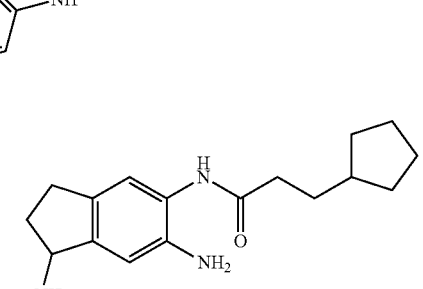

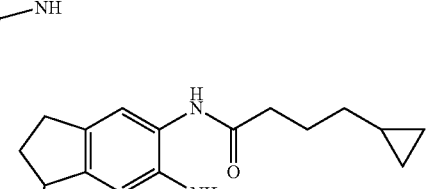

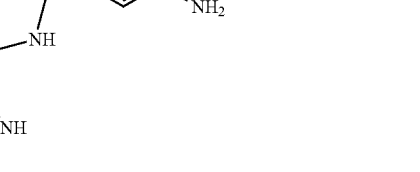

21
-continued
22
-continued
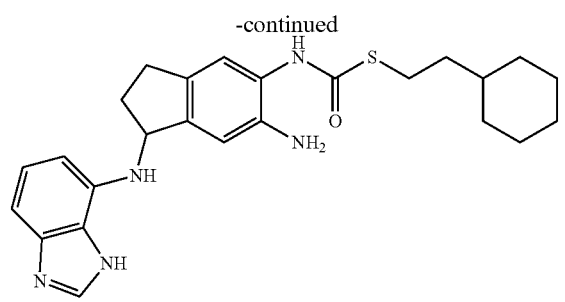

23
-continued
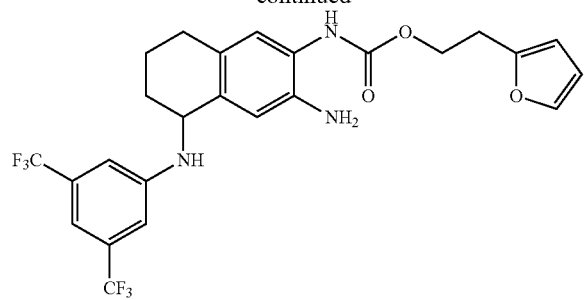
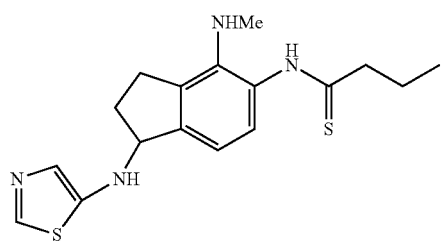
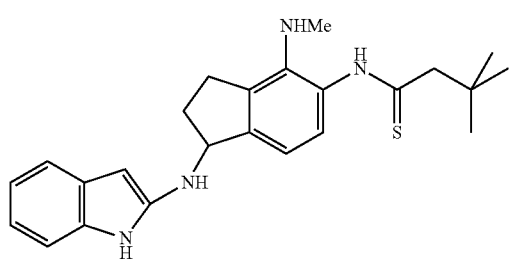
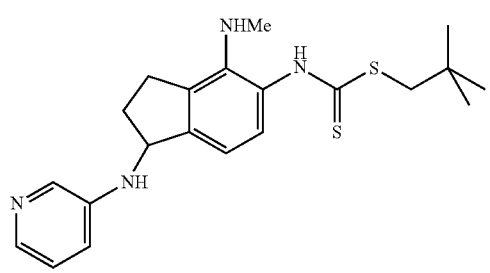
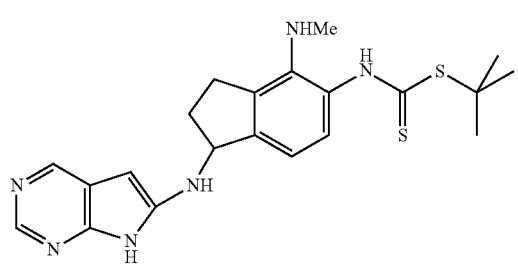
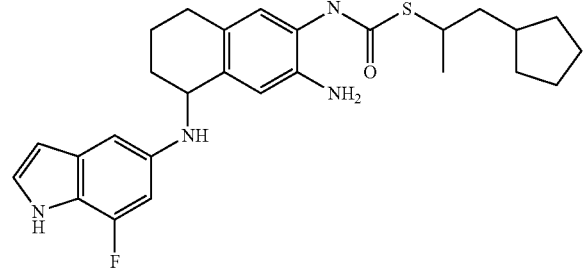
24
-continued
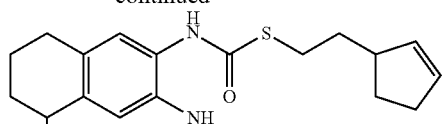
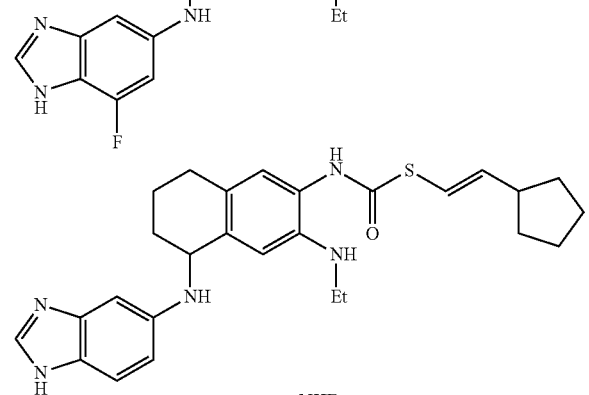
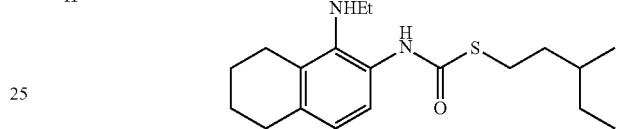
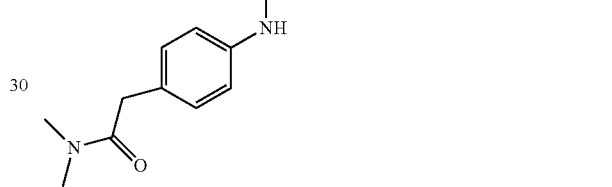
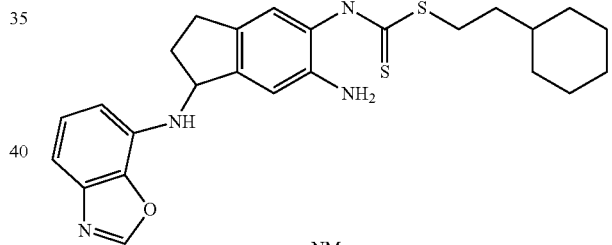
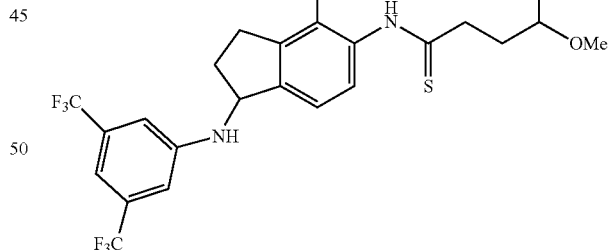
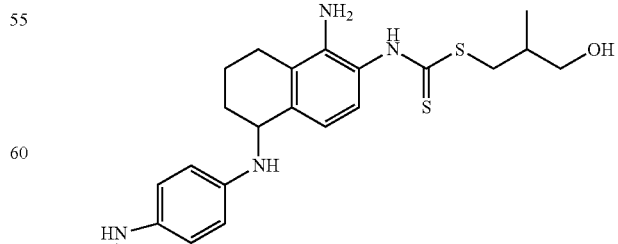

25
-continued
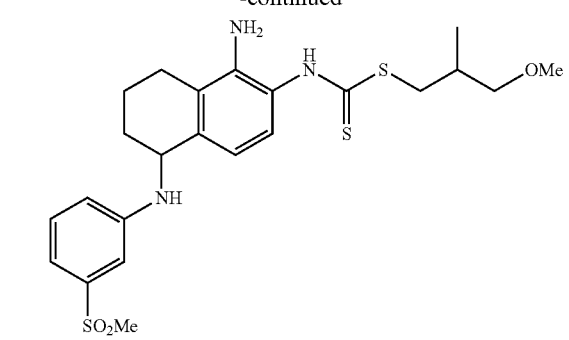
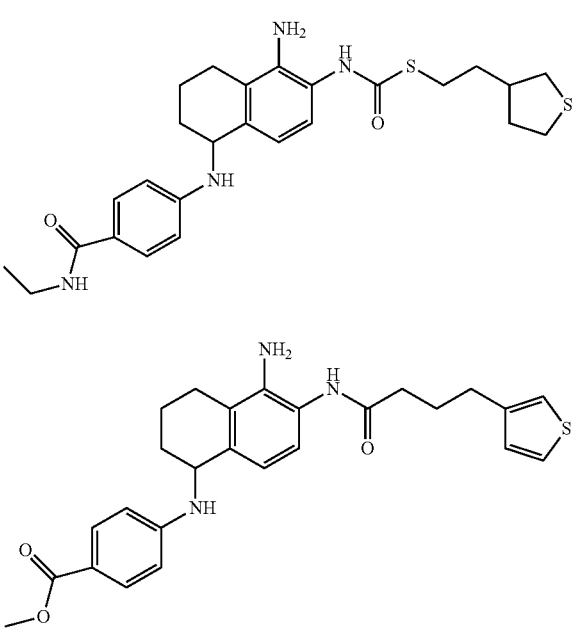
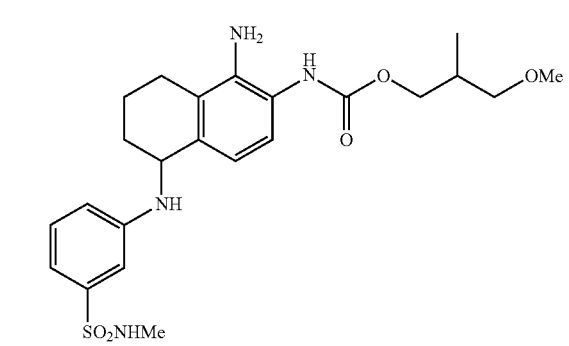
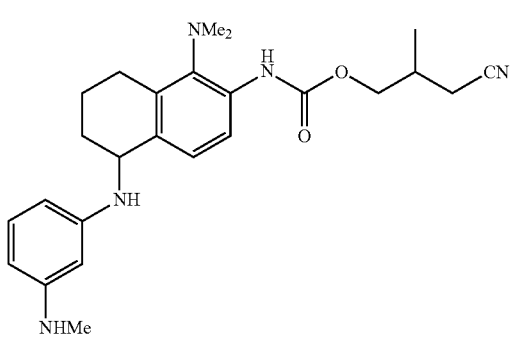
26
-continued
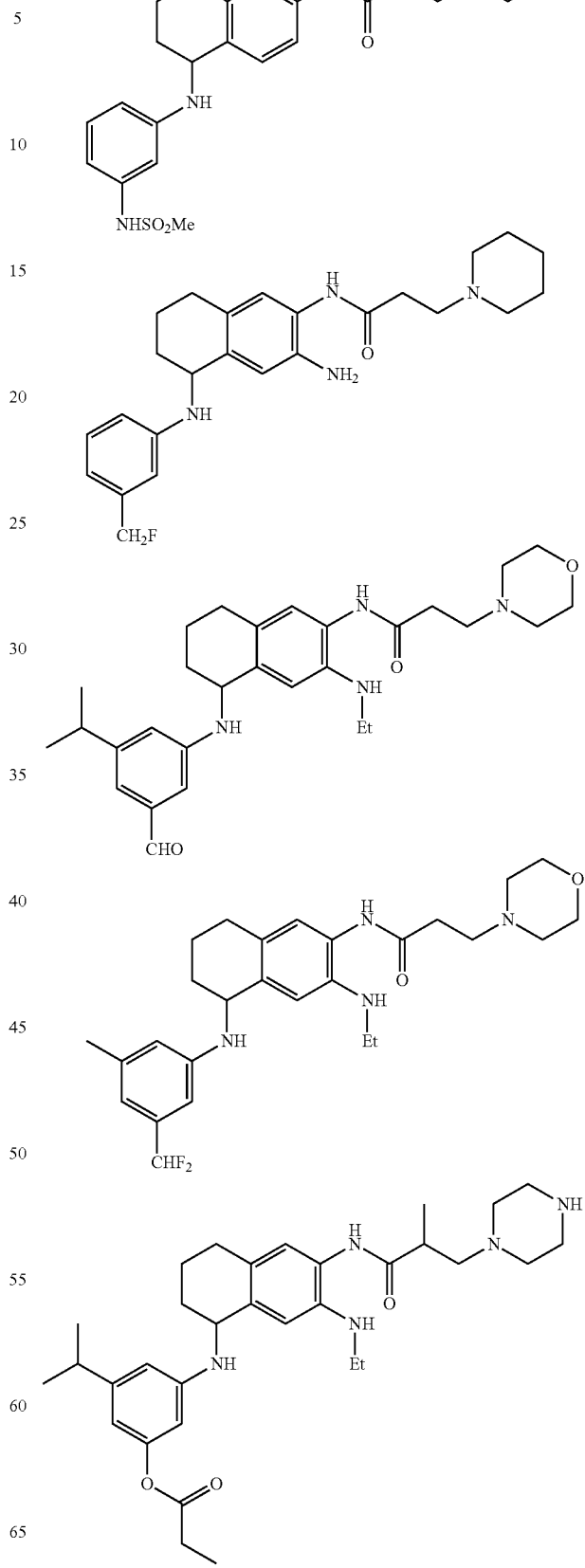

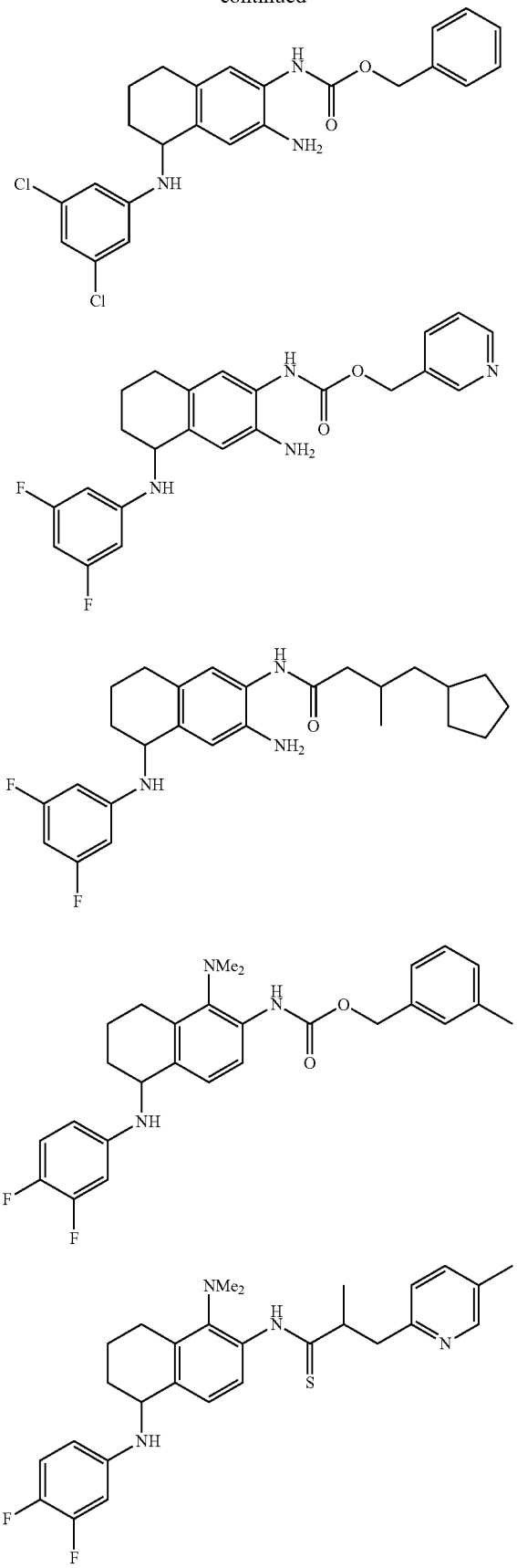

Biological Results

Several typical compounds of this invention were assayed as potassium channel modulators by measuring rhubidium release.

Methods: PC-12 cells were grown at 37° C. and 5% $CO_2$ in DMEM/F12 Medium supplemented with 10% horse serum, 5% fetal bovine serum, 2 mM glutamine, 100 U/ml penicillin, 100 U/ml streptomycin. They were plated in poly-D-lysine-coated 96-well cell culture microplates at a density of 40,000 cells/well and differentiated with 100 ng/ml NGF-7s for 2-5 days. For the assay, the medium was aspirated and the cells were washed once with 0.2 ml in wash buffer (25 mM HEPES, pH 7.4, 150 mM NaCl, 1 mM $MgCl_2$, 0.8 mM $NaH_2PO_4$, 2 mM $CaCl_2$). The cells were then loaded with 0.2 ml $Rb^+$ loading buffer (wash buffer plus 5.4 mM $RbCl_2$, 5 mM glucose) and incubated at 37° C. for 2 h. Attached cells were quickly washed three times with buffer (same as $Rb^+$ loading buffer, but containing 5.4 mM KCl instead of RbCl) to remove extracellular $Rb^+$. Immediately following the wash, 0.2 ml of depolarization buffer (wash buffer plus 15 mM KCl) with or without compounds was added to the cells to activate efflux of potassium ion channels. After incubation for 10 min at room temperature, the supernatant was carefully removed and collected. Cells were lysed by the addition of 0.2 ml of lysis buffer (depolarization buffer plus 0.1% Triton X-100) and the cell lysates were also collected. If collected samples were not immediately analyzed for $Rb^+$ contents by atomic absorption spectroscopy (see below), they were stored at 4° C. without any negative effects on subsequent $Rb^+$ analysis.

The concentration of $Rb^+$ in the supernatants ($Rb^+_{Sup}$) and cell lysates ($Rb^+_{Lys}$) was quantified using an ICR8000 flame atomic absorption spectrometer (Aurora Biomed Inc., Vancouver, B.C.) under conditions defined by the manufacturer. One 0.05 ml samples were processed automatically from microtiter plates by dilution with an equal volume of $Rb^+$ sample analysis buffer and injection into an air-acetylene flame. The amount of $Rb^+$ in the sample was measured by absorption at 780 nm using a hollow cathode lamp as light source and a PMT detector. A calibration curve covering the range 0-5 mg/L $Rb^+$ in sample analysis buffer was generated with each set of plates. The percent $Rb^+$ efflux (F) was defined by $$F=[Rb^+_{Sup}/(Rb^+_{Sup}+Rb^+_{Lys})]\times 100\%$$

The effect (E) of a compound was defined by:
$$E=[(F_c-F_b)/(F_s-F_b)]\times 100\%$$

where the $F_c$ is the efflux in the presence of compound in depolarization buffer, $F_b$ is the efflux in basal buffer, and $F_s$ is the efflux in depolarization buffer, and $F_c$ is the efflux in the presence of compound in depolarization buffer. The effect (E) and compound concentration relationship was plotted to calculate an $EC_{50}$ value, a compound's concentration for 50% of maximal $Rb^+$ efflux.

TABLE 1
ACTIVITIES OF SELECTED COMPOUNDS
legend: A: <0.5 μM; B: 0.5-5 μM; C: >5 μM
| Structure | EC$_{50}$ (μM) |
|---|---|
| 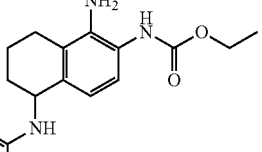 | C |
| 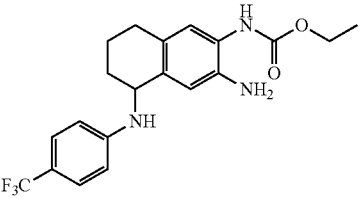 | C |
| 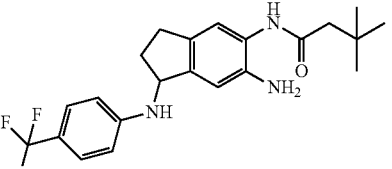 | A |
| 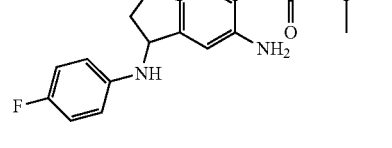 | B |
| 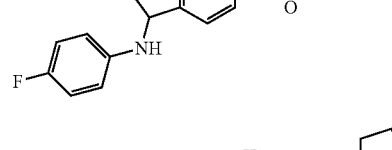 | B |
| 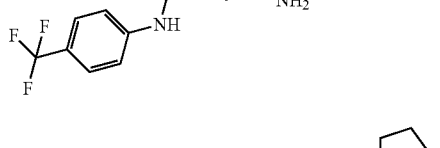 | A |
| 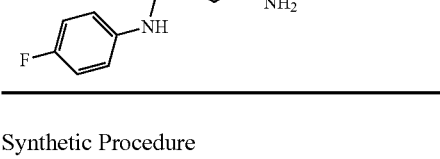 | A |
Synthetic Procedure
Section I. The preparation of compound of formula IX is outlined in Scheme 1.
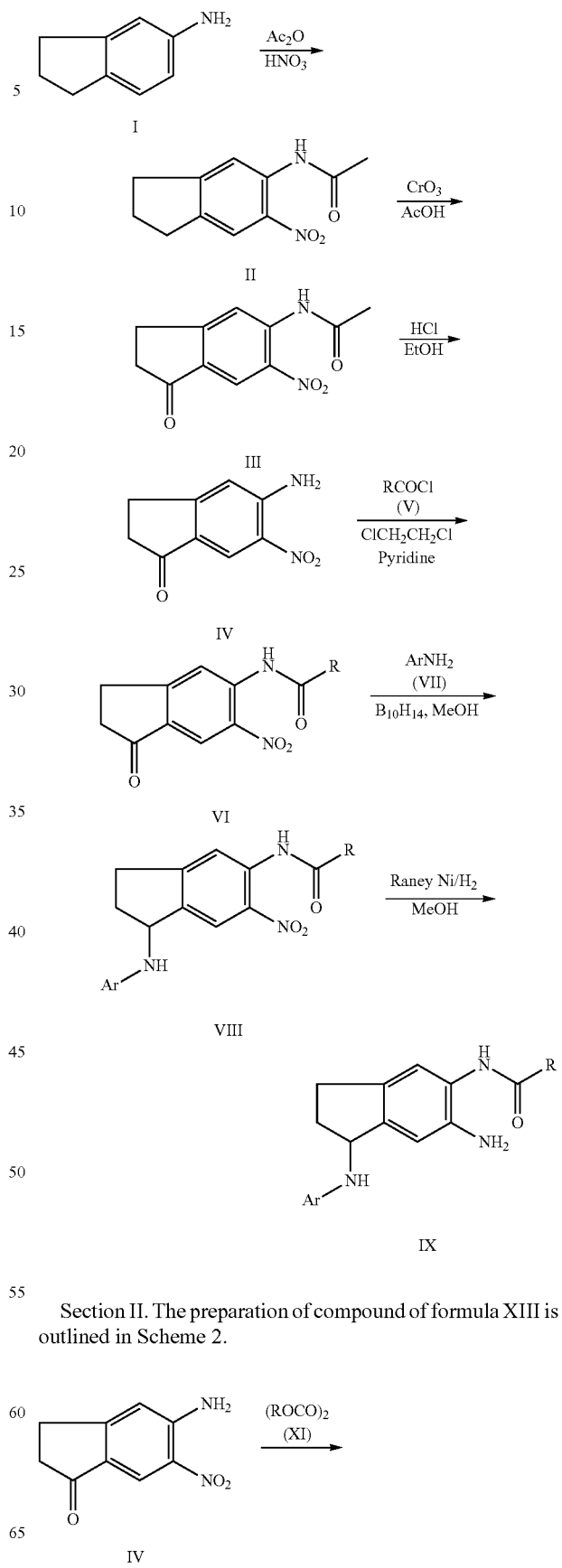
Section II. The preparation of compound of formula XIII is outlined in Scheme 2.

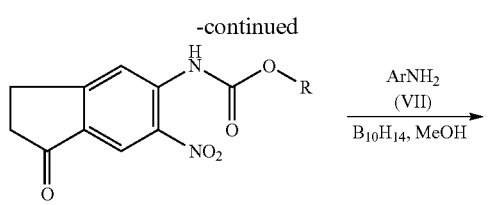
X
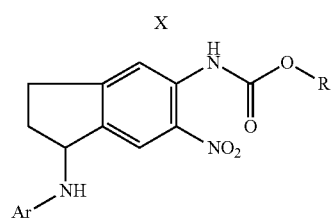
XII
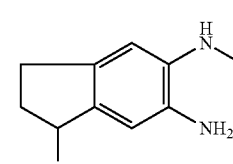
XIII
Section III. The preparation of compound of formula XVIII is outlined in Scheme 3.
XIV
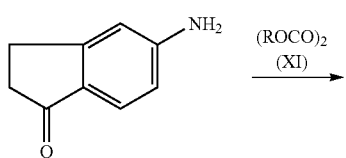
XV
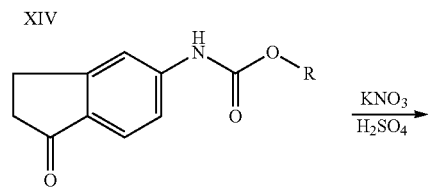
XVI
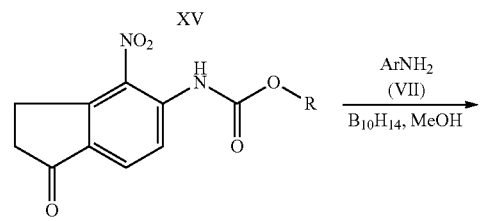
XVII
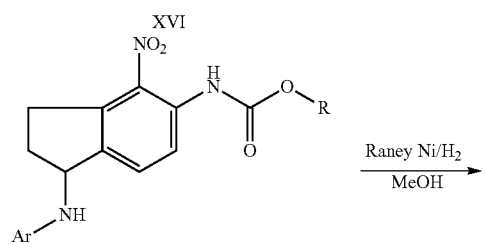
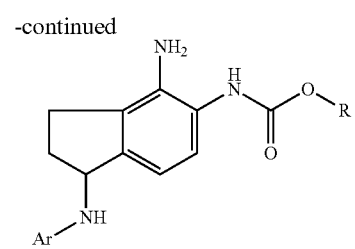
XVIII
Section IV. The preparation of compound of formula XXVI is outlined in Scheme 4.
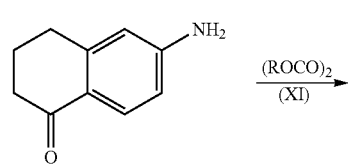
XIX
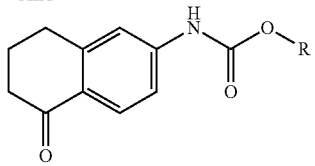
XX
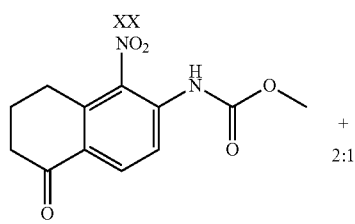
XXI
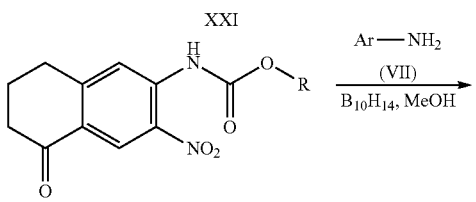
XXII
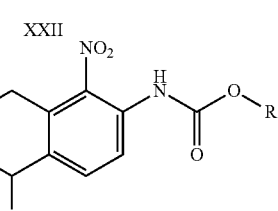
XXIII
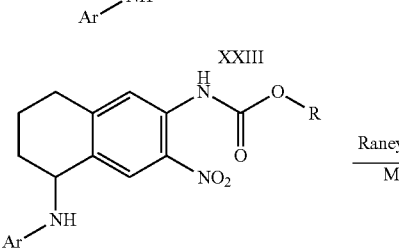
XXIV

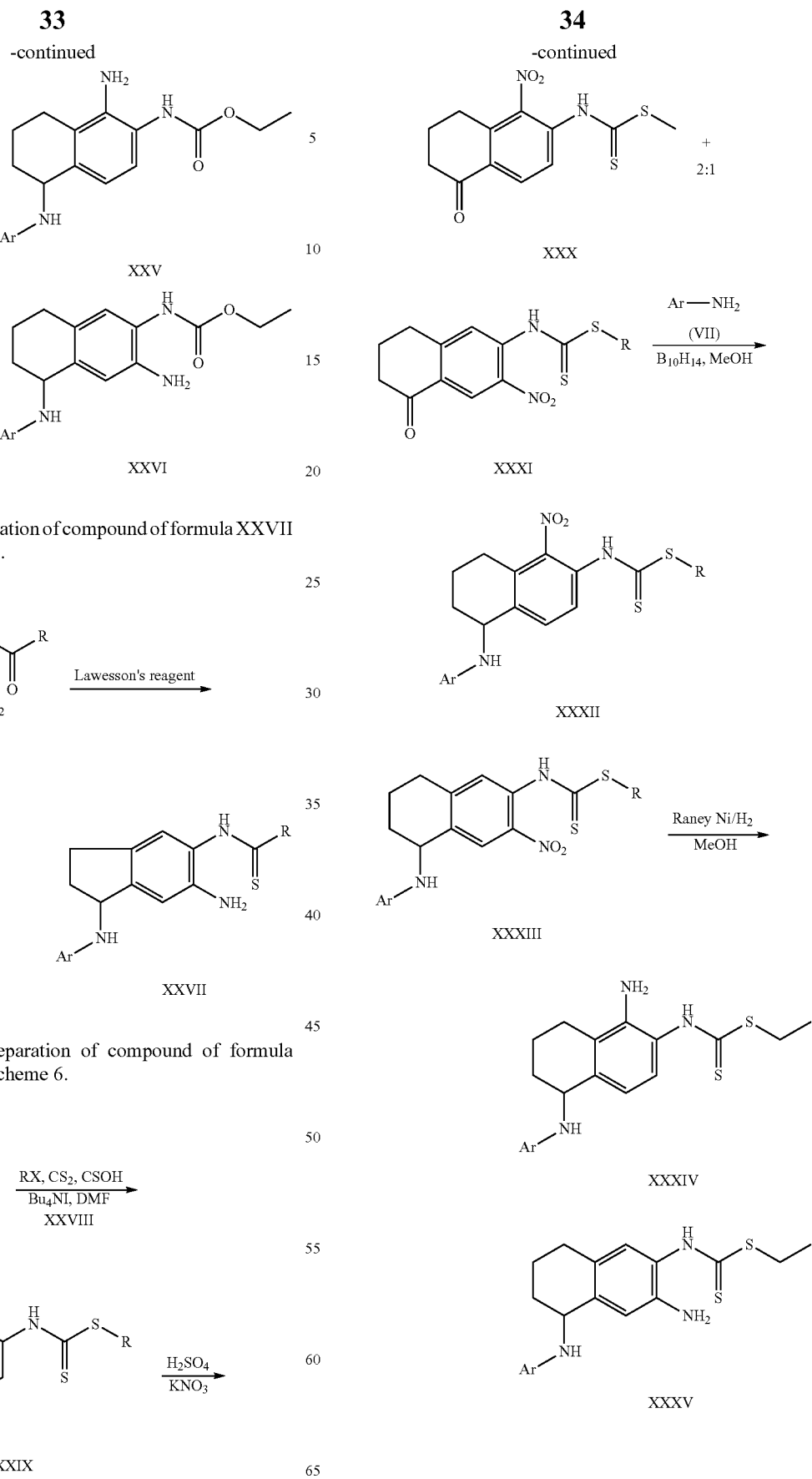
Section V. The preparation of compound of formula XXVII is outlined in Scheme 5.
Section VI. The preparation of compound of formula XXXV is outlined in Scheme 6.
Section VII. The preparation of compound of formula XXXVIII is outlined in Scheme 7.

35

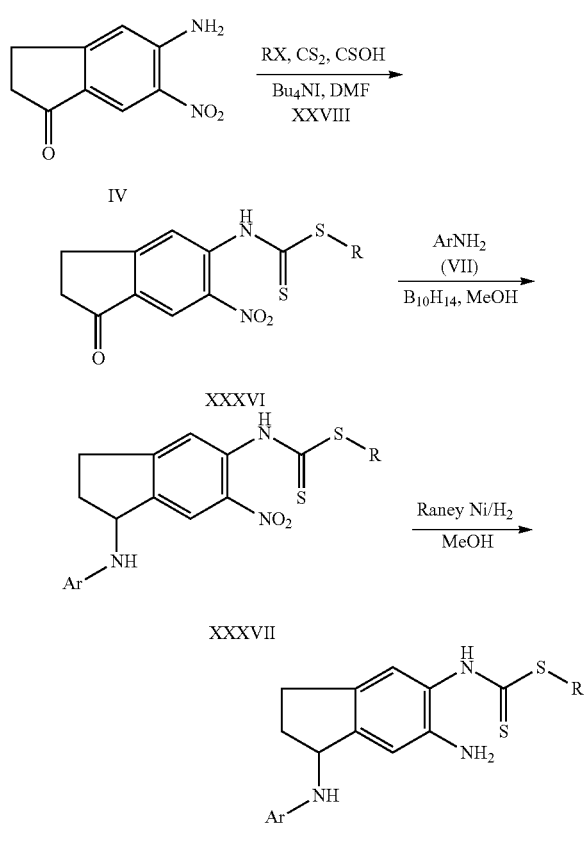

Example 1

Scheme 1

Synthesis of N-[6-Amino-1-(4-trifluoromethyl-phenylamino)-indan-5-yl]-3-cyclopentyl-propionamide

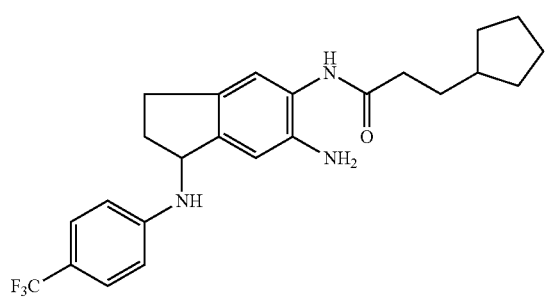

a. N-(6-Nitro-indan-5-yl)-acetamide

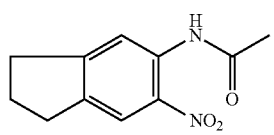

A mixture of 5-aminoindane (13.3 g, 0.1 mol) in 150 ml of acetic anhydride was stirred at room temperature for 3 hours.

36

The reaction mixture was cooled to 0° C., and an ice-cooled solution of 90% nitric acid (d1.4) (8.4 g, 0.12 mol) in 15 ml of acetic anhydride (HNO₃ was added dropwise to acetic anhydride with stirring at 0° C.) was added dropwise. After addition, the reaction mixture was stirred at 0° C. for 1 hour and then at room temperature overnight. The reaction mixture was poured into 800 ml of ice-water with strong stirring. The precipitate was filtered and washed thoroughly with water and dried at 40° C. to give a yellow solid (20.9 g, 95%).

b. N-(6-Nitro-1-oxo-indan-5-yl)-acetamide

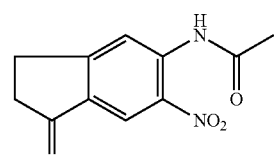

A solution of CrO₃ (26.5 g) in a mixture of 15 ml of H₂O and 235 ml of AcOH was prepared by sonicating the suspension for 45 min. The resulting solution was added dropwise to a cooled solution of N-(6-nitro-indan-5-yl)-acetamide (22 g, 0.1 mol) in Ac₂O (2.5 L) while maintaining the temperature between 15-20° C. After the addition was completed, the mixture was stirred at 25° C. overnight, poured into 10 L of water, and stirred for 1 h. The solution was then extracted with two 2-L portions of CH₂Cl₂. The organic layers were combined, and concentrated to 500 ml, washed with two 50-ml portions of 10% NaOH followed by water, and then dried (Na₂SO₄). The solvent was removed, leaving a yellow powder (16 g, 75%), which was used for next step without further purification.

c. 5-Amino-6-nitro-indan-1-one

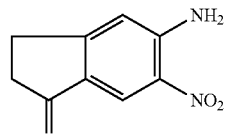

A suspension of N-(6-nitro-1-oxo-indan-5-yl)-acetamide (10 g, 0.042 mol) in HCl (200 ml, 2 N)) and EtOH (100 ml) was refluxed for 30 min. The reaction was cooled to 15° C. and the resulting precipitate was isolated and recrystallized from dilute ethanol to give 7.9 g (97.5%) of yellow solid.

d. N-(6-Nitro-1-oxo-indan-5-yl)-3-cyclopentyl-propionamide

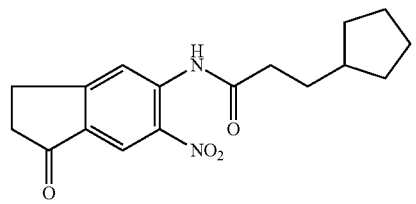

Pyridine (0.1 g, 1.3 mmol) was added to a suspension of 5-amino-6-nitro-indan-1-one (0.19 g, 1 mmol) in 15 ml of anhydrous dichloroethane followed by the addition of 3-cyclopentylpropionyl chloride (0.193 mg, 1.2 mmol) at room temperature under argon. The mixture was stirred at room temperature for 24 hours. The solvent was removed under reduced pressure and the residue was purified by column (hexane/EtOAc, 5:1) to give a yellow solid (0.26 g, 83%). $^1$H-NMR (DMSO-d$_6$): δ 10.47 (s, 1H, NH, exchangeable with D$_2$O), 8.06 (s, 1H), 7.87 (s, 1H), 3.15 (m, 2H), 2.69 (m, 2H), 2.38 (t, 2H, J=7.8Hz), 1.74 (m, 2H), 1.59-1.46 (m, 7H), 1.08 (m, 2H). MS: 317 (M+1).

e. N-[6-Nitro-1-(4-trifluoromethyl-phenylamino)-indan-5-yl]-3-cyclopentyl-propionamide

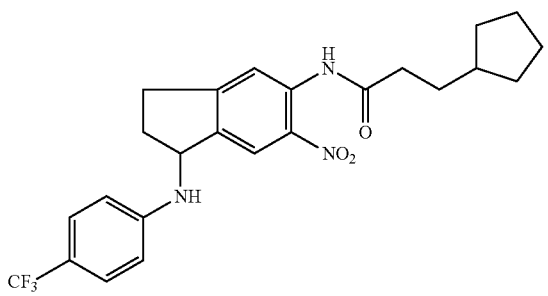

A mixture of N-(6-nitro-1-oxo-indan-5-yl)-3-cyclopentyl-propionamide (0.57 g, 1.8 mmol), 4-trifluoromethylaniline (0.35 g, 2.2 mmol), and decaborane (200 mg) in 20 ml of anhydrous methanol was stirred at room temperature overnight. The solvent was removed in vacuo and the residue was purified by column (hexane/EtOAc, 5:1) to give a pure product (0.65 g, 90%).

f. N-[6-Amino-1-(4-trifluoromethyl-phenylamino)-indan-5-yl]-3-cyclopentyl-propionamide

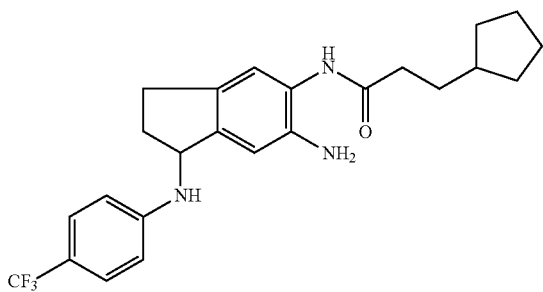

To a solution of N-[6-nitro-1-(4-trifluoromethyl-phenylamino)-indan-5-yl]-3-cyclopentyl-propionamide (200 mg) in 20 ml of methanol was added a catalytic amount of Raney Nickel. The resulting mixture was hydrogenated under regular pressure at room temperature for 4 hours. The reaction mixture was filtered through celite and washed with methanol. The filtrate was evaporated to dryness in vacuo and the residue was purified by column (hexane/EtOAc, 3:1) to give a white solid product in a quantitative yield. $^1$H-NMR (DMSO-d$_6$): δ 9.01 (s, 1H, NH, exchangeable with D$_2$O), 7.36 (d, 2H, J=8.4 Hz), 7.05 (s, 1H), 6.78 (d, 2H, J=8.4 Hz), 6.66 (d, 1H, NH, J=8.4 Hz, exchangeable with D$_2$O), 6.31 (s, 1H), 4.88 (q, 1H, J=8.4 Hz), 4.69 (brs, 2H, NH$_2$, exchangeable with D$_2$O), 2.77 (ddd, 1H, J=15.3, 8.4, 3.6 Hz), 2.67 (m, 1H), 2.42 (m, 1H), 2.29 (t, 2H, J=7.5 Hz), 1.73 (m, 4H), 1.56 (m, 4H), 1.48 (m, 2H), 1.07 (m, 2H). MS: 432 (M+1).

The following compounds were prepared by the above procedure (Scheme 1)

Example 2

N-[6-Amino-1-(4-fluoro-phenylamino)-indan-5-yl]-3-cyclopentyl-propionamide $^1$H-NMR (DMSO-d$_6$): δ 9.01 (s, 1H, NH, exchangeable with D$_2$O), 7.03 (s, 1H), 6.89 (t, 2H, J=9.0 Hz), 6.65 (dd, 2H, J=4.8, 9.0 Hz), 6.64 (s, 1H), 5.73 (d, 1H, NH, J=8.4 Hz, exchangeable with D$_2$O), 4.74 (q, 1H, J=7.2 Hz), 4.66 (brs, 2H, NH$_2$, exchangeable with D$_2$O), 2.75 (ddd, 1H, J=15.0, 8.4, 3.3 Hz), 2.65 (m, 1H), 2.39 (m, 1H), 2.29 (t, 2H, J=7.5 Hz), 1.74 (m, 4H), 1.56 (m, 4H), 1.48 (m, 2H), 1.07 (m, 2H). MS: 382 (M+1).

Example 3

N-[6-Amino-1-(4-fluoro-phenylamino)-indan-5-yl]-3,3-dimethyl-butyramide $^1$H-NMR (DMSO-d$_6$): δ 9.00 (s, 1H, NH, exchangeable with D$_2$O), 7.01 (s, 1H), 6.89 (t, 2H, J=9.0 Hz), 6.65 (dd, 2H, J=4.8, 9.0 Hz), 6.65 (s, 1H), 5.73 (d, 1H, NH, J=8.4 Hz, exchangeable with D$_2$O), 4.74 (q, 1H, J=7.2 Hz), 4.66 (brs, 2H, NH$_2$, exchangeable with D$_2$O), 2.75 (ddd, 1H, J=15.0, 8.4, 3.3 Hz), 2.65 (m, 1H), 2.39 (m, 1H), 2.15 (s, 2H), 1.68 (m, 1H), 1.01 (s, 9H). MS: 356 (M+1).

Example 4

N-[6-Amino-1-(4-trifluoromethyl-phenylamino)-indan-5-yl]-3,3-dimethyl-butyramide $^1$H-NMR (DMSO-d$_6$): δ 9.00 (s, 1H, NH, exchangeable with D$_2$O), 7.35 (d, 2H, J=8.7 Hz), 7.03 (s, 1H), 6.77 (d, 2H, J=8.7 Hz), 6.64 (d, 1H, NH, J=8.4 Hz, exchangeable with D$_2$O), 6.63 (s, 1H), 4.87 (q, 1H, J=7.5 Hz), 4.67 (brs, 2H, NH$_2$, exchangeable with D$_2$O), 2.77 (ddd, 1H, J=15.0, 8.4, 3.3 Hz), 2.65 (m, 1H), 2.40 (m, 1H), 2.15 (s, 2H), 1.73 (m, 1H), 1.00 (s, 9H). MS: 406 (M+1).

Example 5

Scheme 2

Synthesis of ethyl 6-amino-1-(4-fluorophenylamino)-2,3-dihydro-1H-inden-5-ylcarbamate

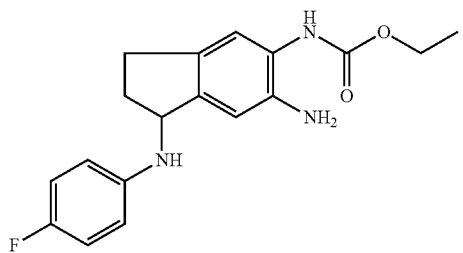

a. Ethyl 6-nitro-1-oxo-2,3-dihydro-1H-inden-5-ylcarbamate

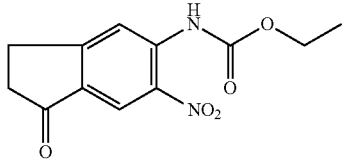

A mixture of 5-amino-6-nitro-2,3-dihydro-1H-inden-1-one (1.19 g, 6.2 mmol), of anhydrous ethanol (15 ml) and diethyl pyrocarbonate (1.2 g, 7.4 mmol) was stirred at room temperature for 3 hours. The solvent was removed in vacuo and the crude product was dried under reduced pressure and used for next step without further purification.

b. Ethyl 1-(4-fluorophenylamino)-6-nitro-2,3-dihydro-1H-inden-5-ylcarbamate

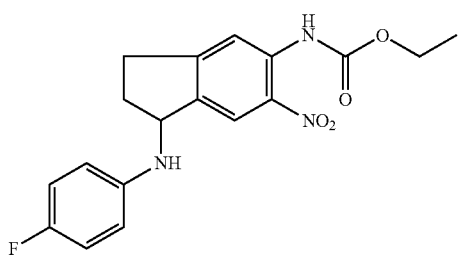

A mixture of ethyl 6-nitro-1-oxo-2,3-dihydro-1H-inden-5-ylcarbamate (0.47 g, 1.8 mmol), 4-fluoroaniline (0.24 g, 2.2 mmol), and decaborane (200 mg) in 20 ml of anhydrous methanol was stirred at room temperature overnight. The solvent was removed in vacuo and the residue was purified by column (hexane/EtOAc, 5:1) to give a pure product (0.51 g, 81%).

c. Ethyl 6-amino-1-(4-fluorophenylamino)-2,3-dihydro-1H-inden-5-ylcarbamate

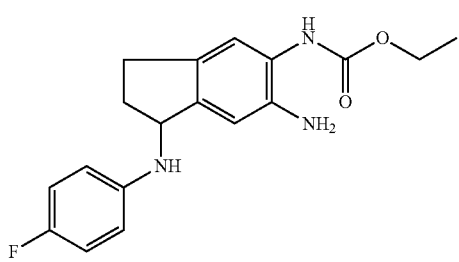

To a solution of ethyl 1-(4-fluorophenylamino)-6-nitro-2,3-dihydro-1H-inden-5-ylcarbamate (250 mg) in 20 ml of methanol was added a catalytic amount of Raney Ni, and the resulting mixture was hydrogenated under ambient temperature and pressure for 4 hours. The reaction mixture was filtered through celite and washed with methanol. The filtrate was evaporated to dryness in vacuo and the residue was purified by column (hexane/EtOAc, 3:1) to give a white solid product. MS: 330 (M+1).

The following compound was prepared by the above procedure (Scheme 2).

Example 6

Scheme 2 ethyl 6-amino-1-(4-(trifluoromethyl)phenylamino)-2,3-dihydro-1H-inden-5-ylcarbamate

MS: 380 (M+1).

Example 7

Scheme 3

Synthesis of [4-Amino-1-(4-fluoro-phenylamino)-indan-5-yl]-carbamic acid ethyl ester

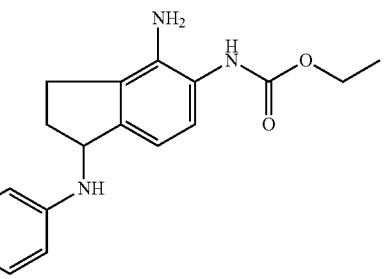

a. (1-Oxo-indan-5-yl)-carbamic acid ethyl ester

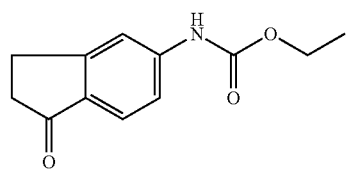

5-Amino-indan-1-one (0.91 g, 6.2 mmol) was dissolved in 15 ml of anhydrous ethanol and diethyl pyrocarbonate (1.2 g, 7.4 mmol) was added dropwise with stirring at room temperature. After addition, the reaction mixture was stirred at room temperature for 3 hours. The solvent was removed in vacuo and the crude product was dried under reduced pressure and used for next step without further purification.

b. (4-Nitro-1-oxo-indan-5-yl)-carbamic acid ethyl ester

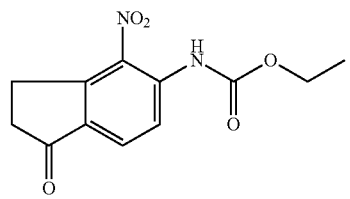

(1-Oxo-indan-5-yl)-carbamic acid ethyl ester (0.94 g, 4.3 mmol) was dissolved in 20 ml of concentrated sulphuric acid and cooled to 0° C. using an ice-bath. Potassium nitrate (477 mg, 4.7 mmol) was added in small portions. After complete addition, the mixture was stirred for 3 hours at 0° C. and then poured onto crushed ice. The yellow precipitate was filtered off, washed thoroughly with water and dried in vacuo to give a yellow solid product (0.85, 75%).

c. [4-Nitro-1-(4-fluoro-phenylamino)-indan-5-yl]-carbamic acid ethyl ester

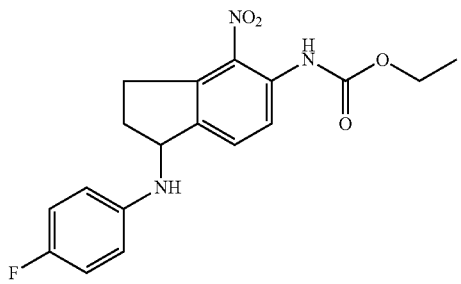

A mixture of (4-nitro-1-oxo-indan-5-yl)-carbamic acid ethyl ester (0.47 g, 1.8 mmol), 4-fluoroaniline (0.24 g, 2.2 mmol), and decaborane (200 mg) in 20 ml of anhydrous methanol was stirred at room temperature overnight. The solvent was removed in vacuo and the residue was purified by chromatography using a mixture of hexane/EtOAc (5:1) as eluant to give a pure product (0.54 g, 83%).

d. [4-Amino-1-(4-fluoro-phenylamino)-indan-5-yl]-carbamic acid ethyl ester

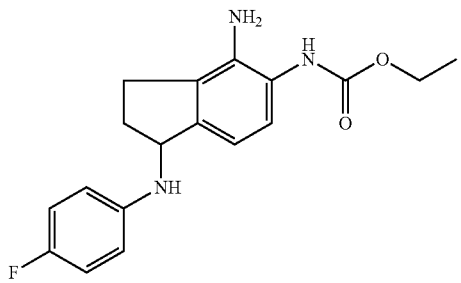

A solution of [4-nitro-1-(4-fluoro-phenylamino)-indan-5-yl]-carbamic acid ethyl ester (200 mg) in 20 ml of methanol was added a catalytic amount of Raney Ni. The resulting mixture was hydrogenated under regular pressure at room temperature for 4 hours. The reaction mixture was filtered through celite and washed with methanol. The filtrate was evaporated to dryness in vacuo and the residue was purified by column (hexane/EtOAc, 3:1) to give a white solid product. $^1$H-NMR (DMSO-$d_6$): δ 8.51 (brs, 1H, NH, exchangeable with $D_2O$), 6.94 (dd, 2H, J=9.0, 18.6 Hz), 6.88 (d, 1H, J=8.1 Hz), 6.66 (dd, 2H, J=4.2, 9.0 Hz), 6.49 (d, 1H, J=8.1 Hz), 5.70 (brs, 1H, NH, exchangeable with $D_2O$), 4.80 (m, 3H, $NH_2$ and CH)), 4.05 (q, 2H, J=7.2 Hz), 2.74 (ddd, 1H, J=3.6, 8.7, 15.6 Hz), 2.60-2.36 (m, 2H), 1.71 (m, 1H), 1.20 (t, 3H, J=7.2 Hz). MS: 330 (M+1).

Example 8

Scheme 4

[1-Amino-5-(4-trifluoromethyl-phenylamino)-5,6,7,8-tetrahydro-naphthalen-2-yl]-carbamic acid ethyl ester

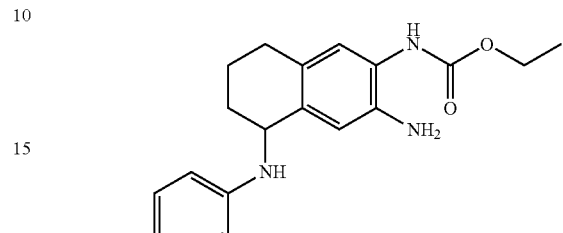

a. (5-Oxo-5,6,7,8-tetrahydro-naphthalen-2-yl)-carbamic acid ethyl ester

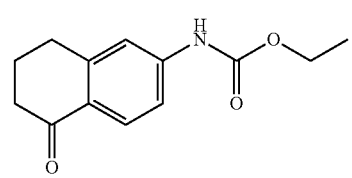

A mixture 6-Amino-3,4-dihydro-2H-naphthalen-1-one (1 g, 6.2 mmol), anhydrous ethanol (15 ml) and diethyl pyrocarbonate (1.2 g, 7.4 mmol) was stirred at room temperature for 3 hours. The solvent was removed in vacuo and the crude product was dried under reduced pressure and used for next step without further purification.

b. (1-Nitro-5-oxo-5,6,7,8-tetrahydro-naphthalen-2-yl)-carbamic acid ethyl ester and (3-Nitro-5-oxo-5,6,7,8-tetrahydro-naphthalen-2-yl)-carbamic acid ethyl ester

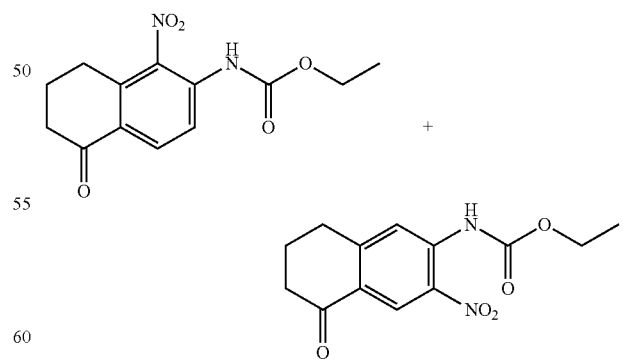

(5-Oxo-5,6,7,8-tetrahydro-naphthalen-2-yl)-carbamic acid ethyl ester (1 g, 4.3 mmol) was dissolved in 20 ml of concentrated sulphuric acid and cooled to 0° C. using an ice-bath. Potassium nitrate (477 mg, 4.7 mmol) was added in small portions. After complete addition, the mixture was stirred for 3 hours at 0° C. and then poured onto crushed ice. The yellow precipitate was filtered off, washed thoroughly with water and dried in vacuo to give the product as a mixture in a 2:1 ratio (0.84 g, 70%).

c. [1-Nitro-5-(4-trifluoromethyl-phenylamino)-5,6,7,8-tetrahydro-naphthalen-2-yl]-carbamic acid ethyl ester and [3-Nitro-5-(4-trifluoromethyl-phenylamino)-5,6,7,8-tetrahydro-naphthalen-2-yl]-carbamic acid ethyl ester

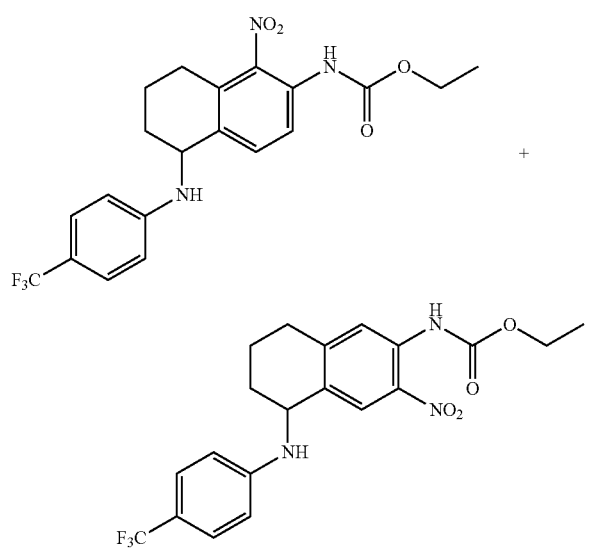

A mixture of (1-nitro-5-oxo-5,6,7,8-tetrahydro-naphthalen-2-yl)-carbamic acid ethyl ester and (3-nitro-5-oxo-5,6,7,8-tetrahydro-naphthalen-2-yl)-carbamic acid ethyl ester (0.5 g, 1.8 mmol), 4-trifluoromethylaniline (0.35 g, 2.2 mmol), and decaborane (200 mg) in 20 ml of anhydrous methanol was stirred at room temperature overnight. The solvent was removed in vacuo and the residue was purified by chromatography using a mixture of hexane/EtOAc (5:1) as eluant to give a pure product as a mixture (0.55 g, 85%).

d. [1-Amino-5-(4-trifluoromethyl-phenylamino)-5,6,7,8-tetrahydro-naphthalen-2-yl]-carbamic acid ethyl ester and [3-Amino-5-(4-trifluoromethyl-phenylamino)-5,6,7,8-tetrahydro-naphthalen-2-yl]-carbamic acid ethyl ester

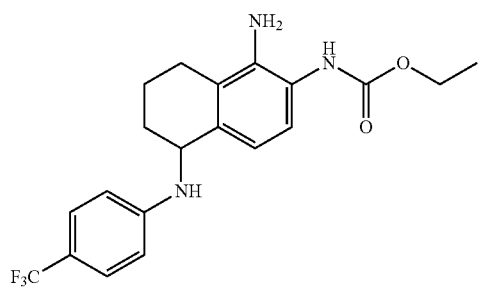

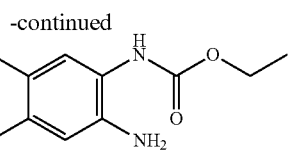

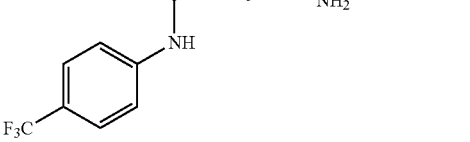

To a solution of a mixture of [1-nitro-5-(4-trifluoromethyl-phenylamino)-5,6,7,8-tetrahydro-naphthalen-2-yl]-carbamic acid ethyl ester and [3-Nitro-5-(4-trifluoromethyl-phenylamino)-5,6,7,8-tetrahydro-naphthalen-2-yl]-carbamic acid ethyl ester (500 mg) in 20 ml of methanol was added a catalytic amount of Raney Ni. The resulting mixture was hydrogenated under regular pressure at room temperature for 4 hours. The reaction mixture was filtered through celite and washed with methanol. The filtrate was evaporated to dryness in vacuo and the residue was separated by preparative HPLC to give two products as white solids in a quantitative yield.

[1-Amino-5-(4-trifluoromethyl-phenylamino)-5,6,7,8-tetrahydro-naphthalen-2-yl]-carbamic acid ethyl ester. $^1$H-NMR (DMSO-$d_6$): δ 8.50 (brs, 1H, NH, exchangeable with $D_2O$), 7.33 (d, 2H, J=8.4 Hz), 6.95 (d, J=8.1 Hz, 1H, exchangeable with $D_2O$), 6.74 (d, 2H, J=8.4 Hz), 6.59 (d, 1H, J=8.1 Hz), 6.49 (d, 1H, J=8.1 Hz), 4.57 (brs, 2H, $NH_2$, exchangeable with $D_2O$), 4.53 (q, 1H, J=8.1 Hz), 4.05 (q, 2H, J=7.2 Hz), 2.43-2.25 (m, 3H), 1.83 (m, 1H), 1.75 (m, 2H), 1.20 (t, 3H, J=7.2 Hz). MS: 394 (M+1).

[3-Amino-5-(4-trifluoromethyl-phenylamino)-5,6,7,8-tetrahydro-naphthalen-2-yl]carbamic acid ethyl ester $^1$H-NMR (DMSO-$d_6$): δ 8.49 (brs, 1H, NH, exchangeable with $D_2O$), 7.33 (d, 2H, J=8.7 Hz), 6.96 (s, 1H), 6.74 (d, 2H, J=8.7 Hz), 6.60 (s, 1H), 6.60 (d, 1H, J=8.1 Hz, exchangeable with $D_2O$), 4.67 (brs, 2H, $NH_2$, exchangeable with $D_2O$), 4.49 (m, 1H), 4.06 (q, 2H, J=7.2 Hz), 2.53 (m, 2H), 1.79 (m, 2H), 1.68 (m, 2H), 1.20 (t, 3H, J=7.2 Hz). MS: 394 (M+1).

The following compound was prepared by the above procedure.

Example 9

Scheme 4

[1-Amino-5-(4-fluoro-phenylamino)-5,6,7,8-tetrahydro-naphthalen-2-yl]-carbamic acid ethyl ester $^1$H-NMR ($CDCl_3$): δ 7.09 (d, 1H, J=8.1 Hz), 6.89 (m, 3H), 6.58 (m, 2H), 6.15 (brs, 1H, NH, exchangeable with $D_2O$), 4.49 (m, 1H), 4.22 (q, 1H, J=6.9 Hz), 3.76 (brs, 3H, $NH_2$ and NH, exchangeable with $D_2O$), 2.54 (m, 2H), 1.94 (m, 4H), 1.31 (t, 3H, J=6.9 Hz). MS: 344 (M+1).

What is claimed is:
1. A method of treating seizure disorders which are affected by modulation of potassium channels, comprising administering to a patient a pharmaceutical composition comprising a pharmaceutically acceptable carrier and a compound of formula I or a salt or ester thereof:

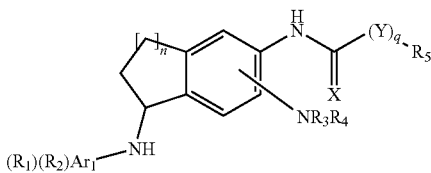

I where Ar₁ is a 5- to 10-member mono- or bicyclic aromatic group, optionally containing 1-4 heteroatoms selected independently from N, O, and S; $R_1$ and $R_2$ are selected, independently, from H, CN, halogen, $CH_2CN$, OH, $NO_2$, $CH_2F$, $CHF_2$, $CF_3$, $CF_2CF_3$, $C_1$-$C_6$ alkyl, $OR_8$, $C(=O)R_9$, $C(=O)OR_{10}$, $OC(=O)R_{11}$, $SR_{12}$, $NR_{13}C(=O)R_{14}$, $C(=O)NR_{15}R_{16}$, $CH_2C(=O)NR_{15}R_{16}$, $NR_{17}R_{18}$, $SO_2R_{19}$, $N(R_{20})SO_2R_{21}$, $SO_2NR_{22}R_{23}$, $C_3$-$C_6$ cycloalkyl, $C_5$-$C_6$ cycloalkenyl, $C_2$-$C_6$ alkenyl, or $C_2$-$C_6$ alkynyl; where the —$NR_3R_4$ group is situated ortho to the NHC(=X) group and $R_3$ and $R_4$ are, independently, H or $C_{1-6}$ alkyl, which $C_{1-6}$ alkyl group optionally substituted with 1 or 2 groups selected, independently, from methyl, halogen, methoxy, and hydroxy, or $R_3$ and $R_4$ together form a 5- or 6-membered ring, optionally substituted with halogen, methyl, methoxy, or hydroxy and optionally containing one or two double bonds; n=1 or 2; X=O or S; Y is O or S; q=1 or 0; $R_5$ is $C_1$-$C_6$ alkyl, $(CHR_6)_wC_3$-$C_6$ cycloalkyl, $(CHR_6)_wCH_2C_3$-$C_6$ cycloalkyl, $CH_2(CHR_6)_wC_3$-$C_6$ cycloalkyl, $(CHR_6)_wC_5$-$C_6$ cycloalkenyl, $CH_2(CHR_6)_wC_5$-$C_6$ cycloalkenyl, $C_2$-$C_6$ alkenyl, $C_2$-$C_6$ alkynyl, $Ar_2$, $(CHR_6)_wAr_2$, $CH_2(CHR_6)_wAr_2$, or $(CHR_6)_wCH_2Ar_2$, where w=0-3, $Ar_2$ is a 5- to 10-member mono- or bicyclic aromatic group, optionally containing 1-4 ring heteroatoms selected independently from N, O, and S; $R_6$ is $C_1$-$C_3$ alkyl; and $R_8$-$R_{23}$ are, independently, H, $C_1$-$C_6$ alkyl, $C_3$-$C_6$ cycloalkyl, $(CHR_6)_wC_3$-$C_6$ cycloalkyl, $C_2$-$C_6$ alkenyl, $C_2$-$C_6$ alkynyl, where all said alkyl, cycloalkyl, alkenyl, alkynyl, aryl, groups are optionally substituted with one or two substituents selected independently from $C_1$-$C_3$ alkyl, halogen, OH, OMe, CN, $CH_2F$, and trifluoromethyl; where, additionally, said alkenyl and alkynyl groups are optionally substituted with phenyl or $C_3$-$C_6$ cycloalkyl; and where all said cycloalkyl groups optionally contain one or two ring heteroatoms selected independently from N, O, and S.

2. The method of claim 1, where NH—C(=X)—(Y)$_q$—R₅ is NHC(=O)R₅ or NHC(=O)OR₅.

3. The method of claim 2, where Ar₁ is

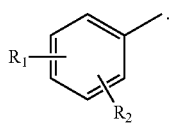

4. The method of claim 3, where $R_1$ is F, $CH_2F$, $CHF_2$, or $CF_3$.

5. The method of claim 4, where n is 1 and $R_1$ is para.

6. The method of claim 4, where $R_2$ is H, $C_1$-$C_3$ alkyl, or halogen.

7. The method of claim 4, where n is 1 and $R_1$ is meta.

8. The method of claim 7, where $R_2$ is H, $C_1$-$C_3$ alkyl, or halogen.

9. The method of claim 1, where the compound of formula I is a compound of formula IA

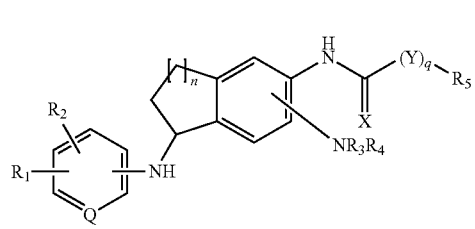

IA where Q=CR₇ or N, where R₇ is H or $C_1$-$C_6$ alkyl.

10. The method of claim 9, where the compound of formula IA is a compound of formula IA-1 or a compound of formula IA-2

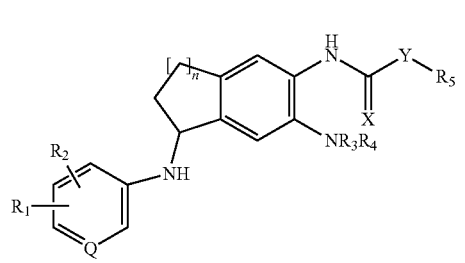

IA-1

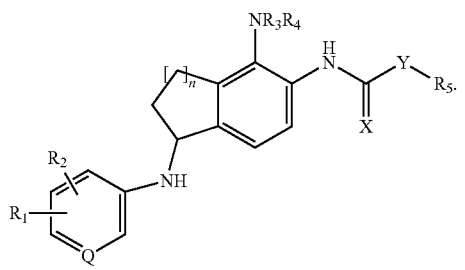

IA-2

11. The method of claim 9, where the compound of formula IA is a compound of formula IA-3 or a compound of formula IA-4

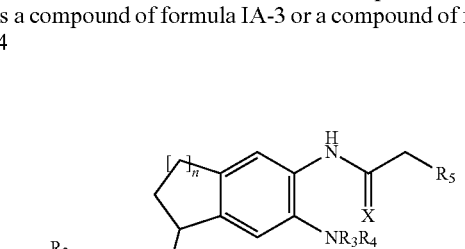

IA-3

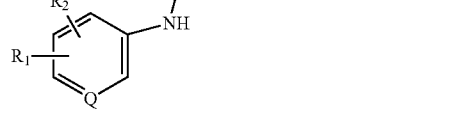

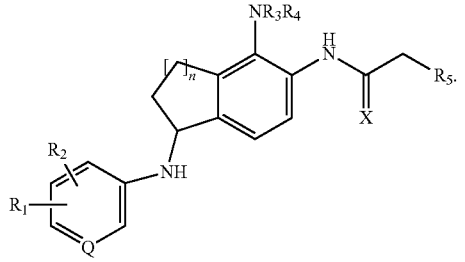

IA-4

12. The method of claim 10, where Q is N; $R_2$, $R_3$, and $R_4$ are, independently, H or $CH_3$; and $R_5$ is $C_1$-$C_6$ alkyl or $(CHR_6)_wC_3$-$C_6$ cycloalkyl, where $R_6$ is H or $CH_3$ and w is 1 or 2.

13. The method of claim 10, where Q is CH; $R_2$, $R_3$, and $R_4$ are, independently, H, $CH_3$ or $CH_2CH_3$; and $R_5$ is $C_1$-$C_6$ alkyl or $(CHR_6)_w C_3$-$C_6$ cycloalkyl, where $R_6$ is H or $CH_3$ and w is 1 or 2.

14. The method of claim 11, where Q is N, $R_2$ and $R_3$ are H, $R_4$ is H or $CH_3$, and $R_5$ is $C_1$-$C_6$ alkyl or $(CHR_6)_w C_3$-$C_6$ cycloalkyl, where $R_6$ is H or $CH_3$ and w is 1 or 2.

15. The method of claim 11, where Q is CH, $R_2$ and $R_3$ are H, $R_4$ is H or $CH_3$, and $R_5$ is $C_1$-$C_6$ alkyl, or $(CHR_6)_w C_3$-$C_6$ cycloalkyl, where $R_6$ is H or $CH_3$ and w is 1 or 2.

16. The method of claim 12, where $R_1$ is meta or para to NH and is halogen or methyl or ethyl, said methyl or ethyl optionally substituted with 1-3 fluorine atoms.

17. The method of claim 13, where $R_1$ is meta or para to NH and is halogen or methyl or ethyl, said methyl or ethyl optionally substituted with 1-3 fluorine atoms.

18. The method of claim 14, where $R_1$ is meta or para to NH and is halogen or methyl or ethyl, said methyl or ethyl optionally substituted with 1-3 fluorine atoms.

19. The method of claim 15, where $R_1$ is meta or para to NH and is halogen or methyl or ethyl, said methyl or ethyl optionally substituted with 1-3 fluorine atoms.

20. The method of claim 1, wherein the compound is one of the following:

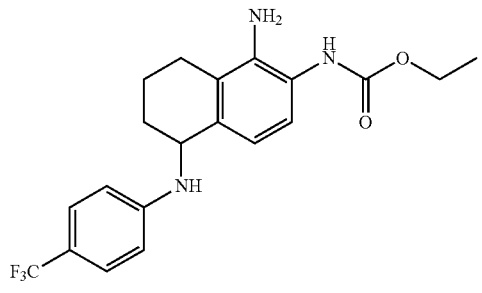

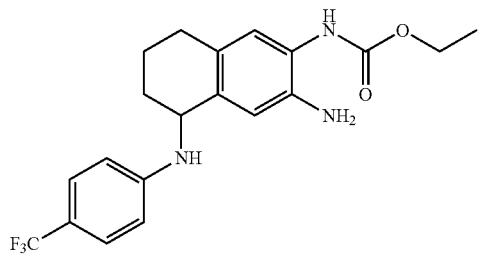

-continued

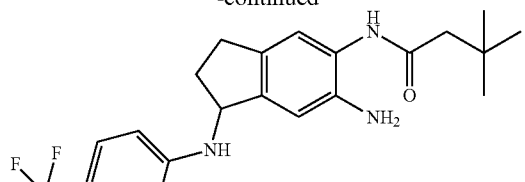

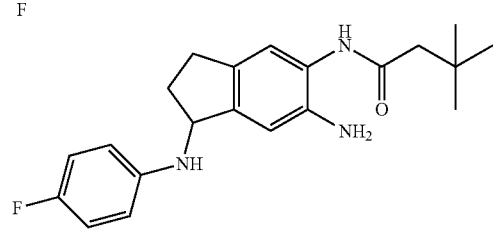

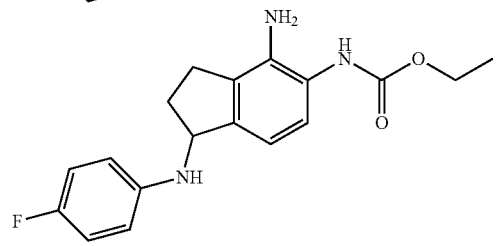

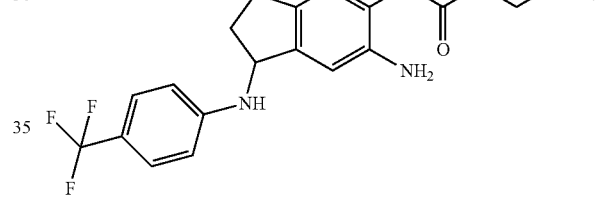

and

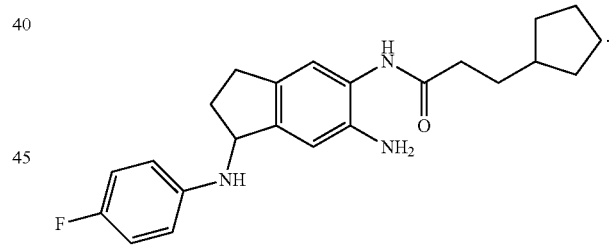

* * * * *